United States Patent
Johnsen

(10) Patent No.: US 10,247,643 B1
(45) Date of Patent: *Apr. 2, 2019

(54) SYSTEM, METHOD, AND APPARATUS FOR DETERMINING AIR EMISSIONS DURING PIG RECEIVER DEPRESSURIZATION

(71) Applicant: MARKWEST ENERGY PARTNERS, L.P., Denver, CO (US)

(72) Inventor: David Johnsen, Denver, CO (US)

(73) Assignee: MARKWEST ENERGY PARTNERS, L.P., Denver, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 16/190,577

(22) Filed: Nov. 14, 2018

Related U.S. Application Data

(60) Continuation of application No. 16/003,250, filed on Jun. 8, 2018, now Pat. No. 10,168,255, which is a
(Continued)

(51) Int. Cl.
  *G01N 1/22* (2006.01)
  *G01N 33/22* (2006.01)
  *F16L 55/46* (2006.01)

(52) U.S. Cl.
  CPC ............ *G01N 1/2247* (2013.01); *F16L 55/46* (2013.01); *G01N 33/225* (2013.01); *G01N 2001/2238* (2013.01)

(58) Field of Classification Search
  None
  See application file for complete search history.

(56) References Cited

U.S. PATENT DOCUMENTS 3,303,525 A   2/1967   Peoples
3,809,113 A   5/1974   Grove
(Continued)

FOREIGN PATENT DOCUMENTS

CN   103497804   1/2014
GB   1179978     2/1970

OTHER PUBLICATIONS

Douglas Daniel Sampaio Santana, et al., "Estimation of trajectories of pipelines PIGs using inertial measurements and non linear sensor fusion," Industry Applications (INDUSCON), 2010 9th IEEE/IAS International Conference, Sao Paulo, Brazil, Nov. 8-10, 2010, http://ieeexplore.ieee.org/xpl/login.jsp?tp=&arnumber=5739911&url=http%3A%2F%2Fieeexplore.ieee.org%2Fxpls%2Fabs_all.jsp%3Farnumber%3D5739911, abstract only.
(Continued)

*Primary Examiner* — Daniel S Larkin
(74) *Attorney, Agent, or Firm* — Hogan Lovells US LLP

(57) ABSTRACT

System, method, and apparatus embodiments characterize potential air emissions during the pig receiver depressurization. The mass flow rate, pressure, and temperature of exhaust gas released from the pig receiver are ascertained using a mass flow meter, pressure gauge, and temperature gauge, respectively. A flow meter and control valve regulate flow of exhaust gas through a sampling line and into a grab sample collection train. The grab sample collection train includes grab sample containers (e.g., piston cylinders, double-ended cylinders, and evacuated canisters) that collect exhaust gas samples over a range of pressures. The exhaust gas samples are used to determine the concentrations of gas components in the exhaust gas over the range of pressures. These concentrations are interpolated and/or extrapolated to provide a concentration versus pressure curve for each identified component in the exhaust gas. The ascertained mass flow rate and gas concentration curve are used to
(Continued)

characterize potential mass emissions of each gas component during pig receiver depressurization.

24 Claims, 41 Drawing Sheets

Related U.S. Application Data division of application No. 15/626,109, filed on Jun. 17, 2017, now Pat. No. 10,024,768.

(60) Provisional application No. 62/351,852, filed on Jun. 17, 2016, provisional application No. 62/412,575, filed on Oct. 25, 2016.

(56) References Cited

U.S. PATENT DOCUMENTS

| | | | |
|---|---|---|---|
| 3,961,493 | A | 6/1976 | Nolan, Jr. |
| 4,073,303 | A | 2/1978 | Foley, Jr. |
| 4,457,037 | A | 7/1984 | Rylander |
| 5,595,709 | A | 1/1997 | Klemp |
| 5,962,774 | A | 10/1999 | Mowry |
| 6,022,421 | A | 2/2000 | Bath |
| 6,834,531 | B2 | 12/2004 | Rust |
| 7,749,308 | B2 | 7/2010 | McCully |
| 7,815,744 | B2 | 10/2010 | Abney et al. |
| 8,312,584 | B2 | 11/2012 | Hodde |
| 8,413,484 | B2 | 4/2013 | Lubkowitz |
| 9,175,235 | B2 | 11/2015 | Kastner |
| 9,310,016 | B2 | 4/2016 | Hodde |
| 9,329,066 | B2 | 5/2016 | Skarping |
| 9,518,693 | B2 | 12/2016 | Hodde |
| 10,024,768 | B1 | 7/2018 | Johnsen |
| 2006/0125826 | A1 | 6/2006 | Lubkowitz |
| 2012/0185220 | A1 | 7/2012 | Shippen |
| 2013/0125323 | A1 | 5/2013 | Henderson |
| 2014/0176344 | A1 | 6/2014 | Littlestar |
| 2014/0345370 | A1 | 11/2014 | Marotta |
| 2015/0323119 | A1 | 11/2015 | Giunta |
| 2016/0091467 | A1 | 3/2016 | Morris |
| 2016/0169436 | A1 | 6/2016 | Sander et al. |
| 2016/0175634 | A1 | 6/2016 | Radian |
| 2016/0363249 | A1 | 12/2016 | Disher |
| 2016/0369930 | A1 | 12/2016 | Poe et al. |

OTHER PUBLICATIONS

Ferdinando Felli, et al., "Structural Health Monitoring of Pipelines for Environment Pollution Mitigation," ASME 2015 Conference on Smart Materials, Adaptive Structures and Intelligent Systems, vol. 2: Integrated System Design and Implementation; Structural Health Monitoring; Bioinspired Smart Materials and Systems; Energy Harvesting, Colorado Springs, CO, USA, Sep. 21-23, 2015, http://proceedings.asmedigitalcollection.asme.org/proceeding.aspx?articleid=2481537, abstract only.

Gerhard Geiger, "Pipeline Leak Detection Technologies and Emergency Shutdown Protocols," 2014 10th International Pipeline Conference, vol. 1: Design and Constructions; Environment; Pipeline Automation and Measurement, Calgary, Alberta, Canada, Sep. 29-Oct. 3, 2014, http://proceedings.asmedigitalcollection.asme.org/proceeding.aspx?articleid=2022559, abstract only.

| Pressure(psig) | 984.4 | 885.3 | 788.4 | 692.9 | 593.5 | 495.0 | 389.7 | 293.7 | 194.1 | 95.5 | 89.8 | a3.7 | a1.1 |
|---|---|---|---|---|---|---|---|---|---|---|---|---|---|
| Container | Cyl | Cyl | Cyl | Cyl | Cyl | Cyl | Cyl | Cyl | Cyl | Cyl | Cyl | Can | Can |
| Component | Alkanes and Inert Gases (mol %) | | | | | | | | | | | | |
| Nitrogen + Oxygen | 0.43 | 0.45 | 0.47 | 0.47 | 0.45 | 0.46 | 0.50 | 0.60 | 0.61 | 0.45 | 0.44 | 0.48 | 0.48 |
| Carbon Dioxide | 0.10 | 0.10 | 0.10 | 0.10 | 0.10 | 0.10 | 0.10 | 0.10 | 0.10 | 0.10 | 0.10 | 0.08 | 1.60 |
| Methane | 73.75 | 75.59 | 76.24 | 76.48 | 76.70 | 76.77 | 76.74 | 76.62 | 76.64 | 74.60 | 74.70 | 46.24 | 33.35 |
| Ethane | 15.67 | 15.22 | 15.20 | 15.19 | 15.19 | 15.24 | 15.30 | 15.40 | 15.47 | 16.69 | 16.72 | 26.95 | 21.11 |
| Propane | 6.21 | 5.55 | 5.35 | 5.32 | 5.25 | 5.23 | 5.22 | 5.23 | 5.22 | 5.86 | 5.86 | 17.55 | 26.08 |
| Isobutane | 0.67 | 0.54 | 0.51 | 0.49 | 0.49 | 0.47 | 0.46 | 0.45 | 0.44 | 0.51 | 0.49 | 1.79 | 3.37 |
| n-Butane | 1.93 | 1.53 | 1.39 | 1.32 | 1.27 | 1.24 | 1.21 | 1.18 | 1.14 | 1.29 | 1.25 | 4.73 | 9.76 |
| Isopentane | 0.39 | 0.30 | 0.24 | 0.22 | 0.20 | 0.19 | 0.18 | 0.17 | 0.15 | 0.18 | 0.17 | 0.71 | 1.60 |
| n-Pentane | 0.52 | 0.40 | 0.32 | 0.28 | 0.25 | 0.22 | 0.23 | 0.20 | 0.18 | 0.23 | 0.20 | 1.02 | 1.95 |
| Hexanes Plus | 0.33 | 0.32 | 0.18 | 0.13 | 0.10 | 0.08 | 0.06 | 0.05 | 0.05 | 0.09 | 0.07 | 0.43 | 0.71 |
| Total | 100 | 100 | 100 | 100 | 100 | 100 | 100 | 100 | 100 | 100 | 100 | 100 | 100 |
| Component | BTEX (ppmv) | | | | | | | | | | | | |
| Benzene | 9.9 | 7.7 | 5.4 | 5.9 | 4.3 | 4.7 | 3.6 | 2.3 | 3.5 | 5.9 | 5.7 | * | * |
| Toluene | 11.5 | 6.6 | 3.2 | 3.7 | 2.4 | 3.0 | 1.6 | 1.0 | 5.5 | 5.0 | 6.1 | * | * |
| Ethyl Benzene | 0.5 | 0.2 | 0.1 | 0.1 | 0.1 | 0.1 | <0.1 | <0.1 | 0.4 | 0.2 | 0.3 | * | * |
| m- + p- Xylene | 5.5 | 1.8 | 0.7 | 0.7 | 0.4 | 1.1 | 0.3 | 0.2 | 4.0 | 1.8 | 2.0 | * | * |
| o-Xylene | 0.9 | 0.3 | 0.1 | 0.1 | 0.1 | 0.2 | <0.1 | <0.1 | 0.7 | 0.3 | 0.4 | * | * |

FIG. 8

| Pressure(psig) | 1023 | 891.9 | 793.5 | 694.5 | 496.1 | 492.3 | 391.4 | 294.6 | 193.8 | i97.1 | a3.9 | a1.4 |
|---|---|---|---|---|---|---|---|---|---|---|---|---|
| Container | Cyl | Cyl | Cyl | Cyl | Cyl | Cyl | Cyl | Cyl | Cyl | Cyl | Can | Can |
| Component | \multicolumn{12}{c}{Alkanes and Inert Gases (mol %)} | | | | | | | | | | | |
| Nitrogen + Oxygen | 0.49 | 0.45 | 0.5 | 0.46 | 0.46 | 0.45 | 0.5 | 0.45 | 0.47 | 0.47 | 0.47 | 0.47 |
| Carbon Dioxide | 0.12 | 0.11 | 0.012 | 0.12 | 0.12 | 0.12 | 0.12 | 0.12 | 0.12 | 0.07 | 0.09 | 0.14 |
| Methane | 75.4 | 75.63 | 75.95 | 76.18 | 76.41 | 76.51 | 76.43 | 76.43 | 76.21 | 71.54 | 50.08 | 66.76 |
| Ethane | 15.64 | 15.6 | 15.59 | 15.57 | 15.64 | 15.6 | 15.66 | 15.76 | 15.9 | 17.42 | 24.85 | 19.82 |
| Propane | 5.48 | 5.44 | 5.34 | 5.27 | 5.22 | 5.2 | 5.22 | 5.24 | 5.32 | 6.83 | 16.23 | 8.98 |
| Isobutane | 0.52 | 0.51 | 0.49 | 0.48 | 0.47 | 0.45 | 0.45 | 0.45 | 0.45 | 0.68 | 1.68 | 0.83 |
| n-Butane | 1.49 | 1.44 | 1.35 | 1.31 | 1.22 | 1.21 | 1.19 | 1.17 | 1.17 | 1.80 | 4.66 | 2.21 |
| Isopentane | 0.27 | 0.26 | 0.23 | 0.21 | 0.17 | 0.17 | 0.16 | 0.15 | 0.15 | 0.37 | 0.73 | 0.31 |
| n-Pentane | 0.38 | 0.36 | 0.3 | 0.28 | 0.22 | 0.22 | 0.22 | 0.18 | 0.17 | 0.46 | 0.89 | 0.37 |
| Hexanes Plus | 0.21 | 0.2 | 0.13 | 0.12 | 0.07 | 0.07 | 0.005 | 0.05 | 0.04 | 0.37 | 0.33 | 0.14 |
| Total | 100 | 100 | 100 | 100 | 100 | 100 | 100 | 100 | 100 | 100 | 100 | 100 |
| Component | \multicolumn{12}{c}{BTEX (ppmv)} | | | | | | | | | | | |
| Benzene | 13.9 | 20 | 19.2 | 21 | 7.8 | 8.9 | 5.1 | 4.6 | 4 | * | * | * |
| Toluene | 23.4 | 33.6 | 26.2 | 24 | 5.9 | 7 | 3.4 | 3.1 | 3.6 | * | * | * |
| Ethyl Benzene | 1.0 | 1.3 | 0.8 | 0.7 | 0.2 | 0.2 | 0.1 | 0.1 | 0.2 | * | * | * |
| m- + p- Xylene | 10.0 | 14.7 | 8.3 | 7.1 | 1.7 | 2.1 | 0.9 | 1.1 | 1.8 | * | * | * |
| o-Xylene | 1.5 | 2.4 | 1.4 | 1.1 | 0.3 | 0.4 | 0.2 | 0.2 | 0.4 | * | * | * |

FIG. 9

| Pressure(psig) | 984.4 | 885.3 | 788.4 | 692.9 | 593.5 | 495.0 | 389.7 | 293.7 | 194.1 | 95.5 |
|---|---|---|---|---|---|---|---|---|---|---|
| Container | Cyl | Cyl | Cyl | Cyl | Cyl | Cyl | Cyl | Cyl | Cyl | Cyl |
| Component | Alkanes and Inert Gases (mol %) | | | | | | | | | |
| Nitrogen+Oxygen[a] | 0.48 | 0.48 | 0.48 | 0.48 | 0.48 | 0.48 | 0.48 | 0.48 | 0.48 | 0.48 |
| Carbon Dioxide[a] | 0.10 | 0.10 | 0.10 | 0.10 | 0.10 | 0.10 | 0.10 | 0.10 | 0.10 | 0.10 |
| Methane | 74.65 | 75.27 | 75.27 | 75.76 | 75.87 | 75.87 | 76.06 | 76.86 | 76.21 | 75.20 |
| Ethane | 15.68 | 15.61 | 15.76 | 15.61 | 15.63 | 15.69 | 15.70 | 14.96 | 15.70 | 15.95 |
| Propane | 5.94 | 5.80 | 5.75 | 5.62 | 5.56 | 5.60 | 5.53 | 5.57 | 5.52 | 6.10 |
| Isobutane | 0.56 | 0.53 | 0.51 | 0.49 | 0.47 | 0.48 | 0.47 | 0.46 | 0.45 | 0.50 |
| n-Butane | 1.64 | 1.54 | 1.45 | 1.36 | 1.31 | 1.30 | 1.24 | 1.21 | 1.17 | 1.28 |
| Isopentane | 0.34 | 0.31 | 0.27 | 0.24 | 0.22 | 0.21 | 0.19 | 0.17 | 0.16 | 0.17 |
| n-Pentane | 0.45 | 0.40 | 0.33 | 0.28 | 0.26 | 0.24 | 0.21 | 0.18 | 0.17 | 0.19 |
| 2-Methylpentane | 0.03 | 0.02 | 0.02 | 0.01 | 0.01 | 0.01 | 0.01 | 0.00 | 0.00 | 0.01 |
| n-Hexane | 0.14 | 0.13 | 0.07 | 0.05 | 0.09 | 0.03 | 0.02 | 0.01 | 0.03 | 0.02 |
| Total | 100 | 100 | 100 | 100 | 100 | 100 | 100 | 100 | 100 | 100 |
| Component | BTEX (ppmv) | | | | | | | | | |
| Benzene | 30.56 | 22.70 | 18.18 | 13.15 | 10.37 | 11.55 | 6.50 | 4.75 | 14.57 | 7.66 |
| Toluene | 33.58 | 22.62 | 13.15 | 7.71 | 5.17 | 5.70 | 1.86 | 1.25 | 30.28 | 4.08 |
| Ethyl Benzene | 0.50 | 0.47 | 0.25 | 0.14 | 0.09 | 0.11 | 0.03 | 0.03 | 1.69 | 0.09 |
| m- + p- Xylene | 8.27 | 4.51 | 2.19 | 0.89 | 0.56 | 1.43 | 0.17 | 0.11 | 24.10 | 0.61 |
| o-Xylene | 1.02 | 0.51 | 0.25 | 0.10 | 0.07 | 0.17 | 0.01 | 0.01 | 3.58 | 0.04 |

FIG. 10

| Pressure(psig) | 1023 | 891.9 | 793.5 | 694.5 | 492.3 | 391.4 | 294.6 | 193.8 | 1.4 |
|---|---|---|---|---|---|---|---|---|---|
| Container | Cyl | Cyl | Cyl | Cyl | Cyl | Cyl | Cyl | Cyl | Can |
| Component | Alkanes and Inert Gases (mol %) | | | | | | | | |
| Nitrogen + Oxygen | 1.3 | 0.5 | 0.6 | 0.5 | 0.5 | 0.9 | 0.5 | 1.2 | 10.7 |
| Carbon Dioxide | 0.1 | 0.1 | 0.1 | 0.1 | 0.1 | 0.1 | 0.1 | 0.1 | 0.0 |
| Methane | 76.1 | 76.7 | 77.2 | 73.7 | 77.7 | 77.3 | 77.6 | 77.0 | 39.1 |
| Ethane | 14.3 | 14.5 | 14.3 | 18.3 | 14.3 | 14.3 | 14.5 | 14.1 | 28.3 |
| Propane | 5.6 | 5.7 | 5.5 | 5.2 | 5.4 | 5.4 | 5.5 | 5.6 | 16.1 |
| Isobutane | 0.4 | 0.5 | 0.4 | 0.4 | 0.4 | 0.4 | 0.4 | 0.4 | 0.4 |
| n-Butane | 1.4 | 1.5 | 1.3 | 1.2 | 1.2 | 1.2 | 1.2 | 1.2 | 3.6 |
| Neopentane | 0.0 | 0.0 | 0.0 | 0.0 | 0.0 | 0.0 | 0.0 | 0.0 | 0.3 |
| Isopentane | 0.3 | 0.2 | 0.2 | 0.2 | 0.2 | 0.2 | 0.2 | 0.2 | 0.4 |
| n-Pentane | 0.3 | 0.3 | 0.3 | 0.3 | 0.2 | 0.2 | 0.2 | 0.2 | 0.6 |
| 2-Methylpentane | 0.0 | 0.0 | 0.0 | 0.0 | 0.0 | 0.0 | 0.0 | 0.0 | 0.1 |
| n-Hexane | 0.1 | 0.1 | 0.1 | 0.1 | 0.0 | 0.0 | 0.0 | 0.0 | 0.3 |
| Total | 100 | 100 | 100 | 100 | 100 | 100 | 100 | 100 | 100 |
| Component | BTEX (ppmv) | | | | | | | | |
| Benzene | 9.9 | 12.5 | 6.7 | 6.5 | 4.3 | 2.8 | 2.7 | 3.5 | 0.4 |
| Toluene | 9.1 | 12.7 | 4.3 | 4.6 | 2.1 | 0.7 | 0.8 | 2.2 | 2.2 |
| Ethyl Benzene | 0.2 | 0.3 | 0.0 | 0.0 | 0.0 | 0.0 | 0.0 | 0.0 | 0.0 |
| m- + p- Xylene | 1.4 | 1.9 | 0.4 | 0.7 | 0.4 | 0.2 | 0.2 | 0.4 | 1.7 |
| o-Xylene | 0.2 | 0.4 | 0.1 | 0.1 | 0.1 | 0.0 | 0.0 | 0.1 | 0.3 |

FIG. 11

| Param-eter | Nitrogen + Oxygen | Methane | Ethane | Propane | Isobutane | n-Butane | Isopentane | n-Pentane | Hexanes Plus | Total VOC |
|---|---|---|---|---|---|---|---|---|---|---|
| A | 4.44E-02 | 9.40E+00 | 5.42E-01 | -4.65E+00 | -8.85E-01 | -2.61E+00 | -5.44E-01 | -6.96E-01 | -3.15E-01 | -9.69E+00 |
| B | 4.11E-01 | 1.40E+01 | 2.21E+01 | 3.32E+01 | 5.31E+00 | -7.89E-02 | 3.00E+00 | 3.84E+00 | 1.75E+00 | 6.21E+01 |
| $r^2$ | 0.98 | 1.0 | 0.9 | 0.1 | 0.96 | 0.94 | 9.20E-01 | 9.70E-01 | 9.90E-01 | 9.80E-01 |
| M | 200 | 100 | 100 | 100 | 100 | 100 | 100 | 100 | 100 | 100 |
| a | 7.36E-01 | 4.50E+01 | 2.55E+01 | 1.41E+01 | 1.77E+00 | 4.29E+00 | 7.62E-01 | 9.90E-01 | 3.69E-01 | 1.97E+01 |
| b | 4.80E-05 | 2.01E-01 | -2.51E-02 | -2.76E-02 | -5.59E-03 | -1.15E-02 | -2.47E-03 | -3.36E-03 | -2.96E-05 | -1.35E-02 |
| c | -2.29E-07 | -1.09E-03 | 6.86E-05 | 8.71E-05 | 1.97E-05 | 4.20E-05 | 9.64E-06 | 1.19E-05 | -4.32E-06 | 1.72E-05 |
| d | NA | 2.93E-06 | -8.06E-08 | -1.13E-07 | -2.69E-08 | -5.92E-08 | -1.38E-08 | -1.59E-08 | 1.07E-08 | NA |
| e | NA | -4.19E-09 | 3.31E-11 | 5.25E-11 | 1.29E-11 | 2.97E-11 | 7.21E-12 | 8.19E-12 | -5.33E-12 | NA |
| f | NA | 3.05E-12 | NA | NA | NA | NA | NA | NA | NA | NA |
| g | NA | -8.94E-16 | NA | NA | NA | NA | NA | NA | NA | NA |
| $r^2$ | 0.4 | 0.99 | 0.98 | 0.98 | 0.99 | 0.99 | 0.99 | 0.99 | 0.95 | 0.94 | if $k < m \rightarrow C_{i,k} = A \cdot \ln(k) + B$ if $k \geq m \rightarrow C_{i,k} = g \cdot k^6 + f \cdot k^5 + e \cdot k^4 + d \cdot k^3 + c \cdot k^2 + b \cdot k + a$

FIG. 47

| Parameter | Benzene | Toluene | Ethyl Benzene | m- + p-Xylene | o-Xylene |
|---|---|---|---|---|---|
| a | 4.09E-05 | 4.32E-05 | 2.66E-07 | 1.08E-05 | 2.44E-06 |
| b | -2.84E-07 | -2.46E-07 | -7.19E-09 | 1.27E-08 | -4.27E-09 |
| c | 9.01E-10 | 6.87-10 | 1.28E-11 | -8.70E-11 | 4.26E-12 |
| d | -1.11E-12 | -8.83E-13 | -1.62E-14 | 2.31E-14 | -1.77E-14 |
| e | 4.92E-16 | 4.51E-16 | 1.11E-17 | 6.84E-17 | 1.99E-17 |
| $r^2$ | 0.95 | 0.88 | 0.62 | 0.7 | 0.65 |

$$C_{i,k} = e \cdot k^4 + d \cdot k^3 + c \cdot k^2 + b \cdot k + a$$

FIG. 48

| Param -eter | Nitrogen + Oxygen | Methane | Ethane | Propane | Isobutane | n-Butane | Isopentane | n-Pentane | Hexanes Plus | Total VOC |
|---|---|---|---|---|---|---|---|---|---|---|
| a | 5.07E-01 | 2.75E+01 | 2.66E+01 | 2.61E+01 | 3.58E+00 | 9.92E+00 | 1.94E+00 | 2.39E+00 | 5.07E+00 | 4.53E+01 |
| b | 9.46E-04 | 3.62E-02 | -3.49E-02 | -1.87E-01 | -2.71E-02 | -7.89E-02 | -1.13E-02 | -1.43E-02 | -5.8E-02 | -3.46E-01 |
| c | 1.75E-06 | -1.49E-03 | 1.05E-04 | 8.19E-04 | 1.13E | 3.32E-04 | 3.00E-05 | 3.88E-05 | 2.59E-04 | 1.63E-03 |
| d | 9.65E-10 | 2.81E-06 | -1.27E-07 | -1.62E-06 | -2.14E-07 | -6.35E-07 | -3.12E-08 | -4.10E-08 | -5.73E-07 | -3.79E-06 |
| e | NA | -2.48E-09 | 5.28E-11 | 1.48E-09 | 1.89E-10 | 5.65E-10 | 1.15E-11 | 1.544E-11 | 6.73E-10 | 4.72E-09 |
| f | NA | 8.24E-13 | NA | -5.03E-13 | -6.26E-14 | -1.89E-13 | NA | NA | -3.98E13 | -2.98E-12 |
| g | NA | NA | NA | NA | NA | NA | NA | NA | 9.31E-17 | 7.46E-16 |
| $r^2$ | 0.71 | 1.0 | 0.96 | 0.99 | 1.0 | 1.0 | 0.99 | 0.96 | 0.96 | 1.0 |

$$C_{i,k} = g \cdot k^6 + f \cdot k^5 + e \cdot k^4 + d \cdot k^3 + c \cdot k^2 + b \cdot k + a$$

FIG. 49

| Parameter | Benzene | Toluene | Ethyl Benzene | m- + p-Xylene | o-Xylene |
|---|---|---|---|---|---|
| a | 1.08E-05 | 6.43E-06 | 2.66E-07 | 2.44E-06 | 5.59E-07 |
| b | 2.06E-03 | 3.24E-03 | 3.19E-03 | 3.33E-03 | 2.91E-03 |
| $r^2$ | 0.78 | 0.86 | 0.81 | 0.81 | 0.77 |

$$C_{i,k} = a \cdot e^{bk}$$

FIG. 50

| Para-meter | Methane | Ethane | Propane | Isobutane | n-Butane | Isopentane | n-pentane | 2-Methyl pentane | Hexanes Plus | Total VOC |
|---|---|---|---|---|---|---|---|---|---|---|
| A | 9.97 | 9.46 | -4.60 | -0.82 | -2.78 | -0.03 | -2.71 | -3.66 | 0.68 | 11.06 |
| B | 11.85 | 14.66 | 34.20 | 4.82 | 15.73 | 0.12 | 4.13 | 5.76 | 2.96 | 67.88 |
| $r^2$ | 1.0 | 1.0 | 0.98 | 0.81 | 0.94 | 1.0 | 1.0 | 0.87 | 0.90 | 0.96 |
| M | 100 | 4 | 100 | 100 | 100 | 4 | 4 | 100 | 100 | 100 |
| a | 5.62E+01 | 2.72E+01 | 1.41E+01 | 1.50E+00 | 3.52E+00 | 5.90E-01 | 9.05E-01 | 1.91E-02 | 1.36E-01 | 1.90E+01 |
| b | 1.78E-02 | -6.36E-02 | -1.86E-02 | -1.96E-03 | -8.94E-04 | -1.80E-04 | -2.21E-03 | -4.30E-05 | -3.88E-04 | -6.15E-03 |
| c | -3.39-E-05 | 2.83E-04 | 5.11E-05 | 5.96E-06 | 1.87E-06 | 7.65E-07 | 4.87E-06 | 1.28E-07 | 8.31E-07 | 8.88E-06 |
| d | 1.57E-08 | -5.56E-07 | -5.79E-08 | -7.02E-09 | NA | NA | -2.1E-09 | NA | NA | NA |
| e | NA | 4.98E-10 | 2.37E-11 | 3.05E-12 | NA | NA | NA | NA | NA | NA |
| f | NA | 1.68E-13 | NA | NA | NA | NA | NA | NA | NA | NA |
| $r^2$ | 0.90 | 0.96 | 0.86 | 0.95 | 0.97 | 0.99 | 0.97 | 0.96 | 0.84 | 0.942 |

If $k < m \rightarrow C_{i,k} = A \cdot \ln(k) + B$ if $k \geq m \rightarrow C_{i,k} = f \cdot k^5 + e \cdot k^4 + d \cdot k^3 + c \cdot k^2 + b \cdot k + a$

FIG. 51

| Parameter | Benzene | Toluene | Ethyl Benzene | m- + p- Xylene | o-Xylene |
|---|---|---|---|---|---|
| a | 1.48E-04 | 1.25E-04 | 6.02E-06 | 4.06E-05 | 5.61E-06 |
| b | -8.08E-07 | -4.62E-07 | -1.86E-08 | -1.03E-07 | -1.32E-08 |
| c | 1.47E-09 | 4.86E-10 | 1.56E-11 | 9.25E-11 | 1.10E-11 |
| d | -7.15E-13 | NA | NA | NA | NA |
| $r^2$ | 0.68 | 0.55 | 0.35 | 0.89 | 0.75 |

$$C_{i,k} = d \cdot k^3 + c \cdot k^2 + b \cdot k + a$$

FIG. 52

| Parameter | Methane | Ethane | Propane | Isobutane | n-Butane | Neopentane | Isopentanen | n-Pentane | 2-Methylpentane | Hexanes Plus | Total VOC |
|---|---|---|---|---|---|---|---|---|---|---|---|
| a | 2.57E+01 | 2.50E+01 | 3.12E+01 | 6.54E-01 | 9.98E+00 | 5.70E-01 | 1.73E+00 | 2.29E+00 | 4.80E-01 | 1.22E+00 | 4.80E+01 |
| b | 3.81E-01 | -6.18E-02 | -2.10E-01 | 2.25E-03 | -7.46E-02 | -7.61E-03 | -1.10E-02 | -1.91E-02 | -5.01E-03 | -1.17E-02 | -3.33E-01 |
| c | -1.53E-03 | 3.17E-04 | 8.28E-04 | -3.70E-06 | 3.03E-04 | 4.02E-05 | 3.34E-05 | 7.96E-05 | 2.09E-05 | 4.82E-05 | 1.32E-03 |
| d | 2.87E-06 | -7.08E-07 | -1.51E-06 | 2.06E-09 | -5.65E-07 | -1.05E-07 | -3.95E-08 | -1.50E-07 | -4.02E-08 | -9.15E-08 | -2.43E-06 |
| e | -2.51E-09 | 7.03E-10 | 1.29E-09 | NA | 4.95E-10 | 1.45E-10 | 1.62E-11 | 1.34E-10 | 3.63E-11 | 8.17E-11 | 2.09E-09 |
| f | 8.26E-13 | -2.54E-13 | -4.20E-13 | NA | -1.64E-13 | -1.01E-13 | NA | -4.54E-14 | -1.24E-14 | -2.74E-14 | -6.84E-13 |
| g | NA | NA | NA | NA | NA | 2.77E-17 | NA | NA | NA | NA | NA |
| $r^2$ | 1.0 | 1.0 | 1.0 | 0.87 | 1.0 | 1.0 | 1.0 | 1.0 | 1.0 | 1.0 | 1.0 |

$$C_{i,k} = g \cdot k^6 + f \cdot k^5 + e \cdot k^4 + d \cdot k^3 + c \cdot k^2 + b \cdot k + a$$

FIG. 53

| Parameter | Benzene | Toluene | Ethyl Benzene | m-+ p-Xylene | o-Xylene |
|---|---|---|---|---|---|
| a | 1.39E-04 | 9.47E-05 | 5.72E-07 | 2.59E-05 | 8.60E-07 |
| b | -1.06E-06 | -6.62E-07 | -2.62E-09 | -3.01E-07 | -2.99E-09 |
| c | 2.87E-09 | 1.53E-09 | 3.20E-12 | 1.36E-09 | 3.65E-12 |
| d | -3.04E-12 | -1.30E-12 | NA | -2.83E-12 | NA |
| e | 1.13E-15 | 3.86E-16 | NA | 2.75E-15 | NA |
| f | NA | NA | NA | -9.93E-19 | NA |
| $r^2$ | 0.97 | 0.93 | 0.57 | 0.97 | 0.50 |

$$C_{i,k} = f \cdot k^5 + e \cdot k^4 + d \cdot k^3 + c \cdot k^2 + b \cdot k + a$$

FIG. 54

| Property | Field Test | Test 1 |
|---|---|---|
| Model Inputs | | |
| Volume (ft$^3$)[a] | 80.6 | 80.6 |
| Temperature (°F)[b] | 60 | 60 |
| Pressure (psig)[a] | 1033.3 | 1059.6 |
| Carbon Dioxide (mol %)[a] | 0.086 | 0.085 |
| Nitrogen (mol %)[a] | 0.455 | 0.454 |
| Methane (mol %)[a] | 74.721 | 74.737 |
| Ethane (mol %)[a] | 15.390 | 15.425 |
| Propane (mol %)[a] | 5.800 | 5.814 |
| Isobutane (mol %)[a] | 0.587 | 0.583 |
| n-Butane (mol %)[a] | 1.702 | 1.685 |
| Isopentane (mol %)[a] | 0.322 | 0.313 |
| n-Pentane (mol %)[a] | 0.482 | 0.467 |
| Hexane (mol %)[a] | 0.272 | 0.261 |
| Heptane (mol %)[a] | 0.136 | 0.131 |
| Octane (mol %)[a] | 0.045 | 0.044 |
| Molecular Weight (g/g-mol) | 21.67 | 21.64 |
| Model Outputs | | |
| Compressibility Factor Peng Robinson (-) | 0.7022 | 0.6938 |
| Compressibility Factor Ref Prop 9 (-) | 0.7295 | 0.7212 |

FIG. 55

| Test | Field Test | | | | Test 1 | | | |
|---|---|---|---|---|---|---|---|---|
| | | | Real Gas Law | | | | Real Gas Law | |
| Method | GPA | ASTMc | Peng Robinson | Ref Prop 9 | GPA | ASTMc | Peng Robinson | Ref Prop 9 |
| Compound | Alkanes and Inert Gases (lb) | | | | | | | |
| Nitrogen+Oxygen | 2.92 | 2.97 | 0.81 | 0.78 | 2.82 | 4.58 | 0.84 | 0.81 |
| Carbon Dioxide | 0.83 | 0.94 | 2.75 | 2.65 | 1.11 | 0.63 | 2.85 | 2.75 |
| Methane | 253.3 | 250.7 | 258.6 | 248.7 | 249.7 | 255.21 | 269.0 | 258.8 |
| Ethane | 99.69 | 102.61 | 99.82 | 96.02 | 101.49 | 92.87 | 104.1 | 100.1 |
| Propane | 55.36 | 56.79 | 55.17 | 53.07 | 53.69 | 59.33 | 57.53 | 55.35 |
| Isobutane | 6.83 | 6.23 | 7.36 | 7.08 | 6.55 | 4.71 | 7.61 | 7.32 |
| n-Butane | 18.18 | 17.53 | 21.34 | 20.52 | 17.64 | 17.97 | 21.98 | 21.15 |
| Neopentane | NA | 0.00 | NA | NA | NA | 0.23 | NA | NA |
| Isopentane | 3.59 | 3.31 | 5.01 | 4.82 | 3.48 | 3.38 | 5.07 | 4.88 |
| n-Pentane | 4.59 | 4.11 | 7.50 | 7.21 | 4.52 | 4.19 | 7.56 | 7.28 |
| 2-Methylpentane | NA | 0.17 | NA | NA | NA | 0.38 | NA | NA |
| Hexanes Plus | 2.46 | 0.92 | 9.13 | 8.78 | 2.33 | 1.41 | 9.11 | 8.76 |
| Total VOC | 90.81 | 91.23 | 105.5 | 101.5 | 87.15 | 90.73 | 108.9 | 104.7 |
| Total | 447.7 | 446.3 | 467.4 | 449.7 | 443.3 | 444.9 | 485.7 | 467.2 |
| Compound | BTEX (lb) | | | | | | | |
| Benzene | 7.35E-05 | 2.60E-04 | NA | NA | 1.63E-04 | 1.42E-04 | NA | NA |
| Toluene | 6.38E-05 | 2.47E-04 | NA | NA | 2.24E-04 | 1.11E-04 | NA | NA |
| Ethyl Benzene | 2.82E-06 | 9.02E-06 | NA | NA | 8.92E-06 | 1.51E-06 | NA | NA |
| m- + p-Xylene | 2.60E-05 | 9.03E-05 | NA | NA | 9.08E-05 | 2.07E-05 | NA | NA |
| o-Xylene | 4.26E-06 | 1.22E-05 | NA | NA | 1.53E-05 | 2.66E-06 | NA | NA |

FIG. 56

| Test | Field Test | | | | | | Test 1 | | | | | |
|---|---|---|---|---|---|---|---|---|---|---|---|---|
| | Combined GPA and ASTMc (lb) | Real Gas Law | | | | | Combined GPA and ASTMc (lb) | Real Gas Law | | | | |
| | | Peng Robinson | | Ref Prop 9 | | | | Peng Robinson | | Ref Prop 9 | | |
| Method | | Estimate (lb) | AAE[a] (%) | Estimate (lb) | AAE[a] (%) | | | Estimate (lb) | AAE[a] (%) | Estimate (lb) | AAE[a] (%) | |
| Total VOC | 91.6±4.7 | 105.5 | 15.2 | 101.5 | 10.8 | | 87.6±5.6 | 108.9 | 24.3 | 104.7 | 19.5 | |
| Total Mass | 447.5±1.3 | 467.4 | 4.4 | 449.7 | 0.5 | | 443.5±1.2 | 485.7 | 9.5 | 467.2 | 5.3 | |

FIG. 57

| Property | Field Test | Test 1 |
|---|---|---|
| Total VOC (lb) | 5.1 | 2.0 |
| Total Mass (lb) | 8.0 | 5.5 |

FIG. 58

SYSTEM, METHOD, AND APPARATUS FOR DETERMINING AIR EMISSIONS DURING PIG RECEIVER DEPRESSURIZATION

CROSS REFERENCE TO RELATED APPLICATIONS

This application is a continuation of, and claims priority to and the benefit of, U.S. Non-Provisional application Ser. No. 16/003,250, titled "SYSTEM, METHOD, AND APPARATUS FOR DETERMINING AIR EMISSIONS DURING PIG RECEIVER DEPRESSURIZATION," filed Jun. 8, 2018, now U.S. Pat. No. 10,168,255, issued Jan. 1, 2018, which is a divisional of, and claims priority to and the benefit of, U.S. Non-Provisional application Ser. No. 15/626,109, titled "SYSTEM, METHOD, AND APPARATUS FOR DETERMINING AIR EMISSIONS DURING PIG RECEIVER DEPRESSURIZATION," filed Jun. 17, 2017, now U.S. Pat. No. 10,024,768, issued Jul. 17, 2018, which claims priority to and the benefit of U.S. Provisional Application No. 62/351,852, titled "SYSTEM, METHOD, AND APPARATUS FOR DETERMINING AIR EMISSIONS DURING PIG RECEIVER DEPRESSURIZATION," filed Jun. 17, 2016, and to U.S. Provisional Application No. 62/412,575, titled "SYSTEM, METHOD, AND APPARATUS FOR DETERMINING AIR EMISSIONS DURING PIG RECEIVER DEPRESSURIZATION," filed Oct. 25, 2016, the full disclosures of which are incorporated herein by reference.

BACKGROUND

Field of the Invention

One or more embodiments relate to hydrocarbon transportation equipment and, more particularly, to systems, methods, and apparatuses to characterize air emissions during gas pipeline pig receiver depressurization.

Background

The transportation of hydrocarbons often occurs via pipeline. For instance, the natural gas industry utilizes a network of low-pressure and high-pressure pipelines to transport raw natural gas from well sites to natural gas processing facilities. Unprocessed natural gas is composed primarily of methane, but may also contain ethane, propane, butane, pentane, and heavier components. In part due to the presence of these heavier hydrocarbon components, unprocessed natural gas partially condenses in the pipeline. This partial condensation can occur in pipelines operating at either low pressure or high pressure.

Low-pressure pipelines are the gathering pipelines from the wellhead to the low pressure inlet of a compressor station and such low-pressure pipelines can operate in a pressure range from near-atmospheric pressure to greater than 300 lbs. per square inch gauge (psig). High-pressure pipelines are the pipelines from the discharge of the compressor station to a gas processing plant and such high-pressure pipelines typically operate in a pressure range from about 850 psig to about 1000 psig (i.e., immediately upstream of the gas processing plant).

The flow of liquids and gases (or vapors) in the pipelines is commonly referred to as two-phase flow. If liquid water or glycols are also present, then the pipeline is referred to as having three-phase or multi-phase flow. The presence of liquids can substantially reduce the achievable flow capacity of the pipelines. The amount of liquid residing in the pipeline is commonly referred to as the liquid holdup and is periodically reduced in a process operation known as "pigging".

Pigs are cylindrical-like or spherical devices with the same or near-same inner diameter as the pipeline (i.e., having an outer circumference less than the inner circumference of the inner wall of the pipeline). For example, in the Marcellus gathering system, cylindrical pigs are typically utilized due to their better sweeping efficiency and reliability than spherical pigs. The name "pig" comes from the squealing sound that the pig makes as it moves down the pipeline. The pig cusps or abuttingly glides along at least a portion of the inner wall of the pipeline as it is propelled by the flowing gas and sweeps liquid holdup such that the traversed length of pipeline is temporarily free of any liquids.

Pigs with sensors can also be used when mechanical issues with the pipeline necessitate maintenance on the pipeline. In these cases, maintenance is performed without stopping the hydrocarbon flow through the pipeline. Sensors onboard the pig can gather data on the state of the pipeline and hydrocarbon flow rate at various positions. The pig, being fitted to the particular pipeline in which it is used, can also scrape the interior walls of the pipeline to remove debris. Pigs can be used in other contexts in addition to inspecting and cleaning as noted above.

Pigs are introduced into the pipeline through a piping arrangement called a pig launcher, which has a launcher barrel that is selectively in fluid communication with the pipeline through one or more valves. Pigs are removed through a piping arrangement called a pig receiver, which has a receiver barrel that is selectively in fluid communication with the pipeline through one or more valves to receive the pig from the pipeline. After receipt of the pig, the receiver barrel will contain unprocessed natural gas at the same pressure as the flowing pipeline; therefore, the unprocessed natural gas must be vented so that the operators can safely open the receiver hatch in the pig receiver and remove the pig from the receiver barrel. Pipeline operators remove the pig from the barrel of the pig receiver after first ensuring that it is completely isolated from the flowing pipeline by closed valves. The launcher barrel of the pig launcher must also be vented to remove the high-pressure, unprocessed natural gas that enters the launcher barrel during the insertion of the pig into the pipeline. The pig receiver/launcher gas is typically vented to atmosphere. Disclosed herein are systems and methods to ascertain and measure the air emissions that are exhausted from the pig receiver/launcher during pig receiver/launcher depressurization.

SUMMARY

Systems, methods, and apparatuses for determining or characterizing air emissions during pig receiver depressurization are disclosed. In one or more embodiments, a method to characterize emissions during pig receiver depressurization includes one or more of: isolating pressurized gas flow between a pipeline and a pig receiver having a receiver barrel and a pig disposed therein, controlling a valve in an exhaust gas line to release pressurized gas from the pig receiver as exhaust gas into the exhaust gas line that is in fluid communication with the pig receiver, ascertaining mass flow rate and exhaust pressure of the exhaust gas flowing through the exhaust gas line, obtaining a plurality of exhaust gas samples from a slip stream that is in fluid communication with the exhaust gas line over a range of different exhaust pressures when exhaust gas flows through the exhaust gas line and the slip stream, analyzing each of the plurality of exhaust gas samples to identify a plurality of gas components, and determining a percentage of each gas component identified in each of the plurality of exhaust gas samples. Exhaust gas flow may be controlled through a sampling manifold of a grab sample collection train that is in fluid communication with the slip stream. The grab sample collection train may have a plurality of grab sample containers coupled, e.g., sequentially, along the sampling manifold and selectively in fluid communication therewith to collect, e.g., a first exhaust gas sample in one of the plurality of grab sample containers at a first pressure and a second exhaust gas sample in another of the plurality of grab sample containers at a second pressure lower than the first pressure.

In one or more embodiments, the temperature, pressure and mass flow rate of the exhaust gas released from the pig receiver are ascertained using a temperature sensor, a pressure sensor and a mass flow meter, respectively, each disposed in the exhaust gas line. The flow of exhaust gas into a grab sample collection train via a low flow rate slip stream or sampling line in fluid communication with the exhaust gas line is controlled using a flow meter and a control valve responsive thereto that are disposed downstream of the grab sample collection train. A number of grab samples or exhaust gas samples are collected in the grab sample collection train over a range of depressurization pressures using a plurality of grab sample containers (e.g., selected from the group consisting of sampling piston cylinders, evacuated canisters, and double-ended sampling cylinders). The plurality of exhaust gas samples can be used to generate a gas composition curve that characterizes the composition of the exhaust gas throughout the full range of conditions, such as pressures, temperatures and mass flow rates, that occur during pig receiver depressurization. Interpolation and extrapolation techniques can be used to determine gas compositions at values in between or outside of measured values. Potential mass emissions can be determined for various individual gas components based upon the ascertained mass flow rate of exhaust gas and the generated gas composition curve.

In one or more embodiments, a system to characterize emissions during pig receiver depressurization includes one or more of: a pig receiver in selective fluid communication with a pressurized gas pipeline in which the pig receiver has a receiver barrel with a pig disposed therein, an exhaust gas line coupled to the pig receiver and positioned to accept pressurized gas released from the pig receiver as exhaust gas, a valve disposed in the exhaust gas line to control release of pressurized gas from the pig receiver, a pressure sensor disposed in the exhaust gas line upstream of the valve to measure exhaust pressure of exhaust gas released from the pig receiver, a mass flow meter disposed in the exhaust gas line upstream of the valve to measure mass flow rate of exhaust gas released from the pig receiver, a slipstream in fluid communication with the exhaust gas line that directs a portion of the exhaust gas therethrough such that the slipstream fluidly couples to the exhaust gas line upstream of the valve and downstream of the pressure sensor and mass flow meter, and a grab sample collection train having a sampling manifold in fluid communication with the slip stream. The grab sample collection train may include a plurality of grab sample containers coupled along the sampling manifold and arranged and designed to capture exhaust gas samples from exhaust gas flowing through the sampling manifold over a range of different exhaust pressures as measured by the pressure sensor.

In one or more embodiments, an apparatus to characterize emissions during pig receiver depressurization includes one or more of: a sampling line configured to be fluidly coupled to an exhaust gas line positioned to accept exhaust gas released from a pig receiver such that the exhaust line extends downstream from the pig receiver, a sampling manifold positioned downstream from and in fluid communication with the sampling line, a plurality of piston cylinders coupled sequentially along the sampling manifold through piston cylinder inlet lines and positioned to collect exhaust gas samples of exhaust gas over a range of pressures flowing through the sampling manifold, a piston cylinder inlet valve disposed in each piston cylinder inlet line positioned between each of the plurality of piston cylinders and the sampling manifold and actuated to an open position when collecting exhaust gas therethrough, a plurality of evacuated canisters coupled to the sampling manifold downstream of the piston cylinders through evacuated canister inlet lines and positioned to collect exhaust gas samples of exhaust gas flowing through the sampling manifold at pressures lower than the range of pressures, an evacuated canister inlet valve disposed in each evacuated canister inlet line between each of the plurality of evacuated canisters and the sampling manifold and actuated to an open position when collecting exhaust gas therethrough, and a controller configured to sequentially open and close each piston cylinder inlet valve and each evacuated canister inlet valve in response to pre-selected exhaust gas pressures during pig receiver depressurization.

Further, a control valve may be disposed in a sampling exhaust line in fluid communication with the sampling manifold and downstream thereof to control exhaust gas flow through the sampling manifold, e.g., the exhaust gas flow through the sampling manifold may be controlled to be less than the exhaust gas flow through the exhaust gas line. The control valve may be responsive to a flow meter that is disposed in the sampling exhaust line between the sampling manifold and the control valve. In one embodiment, eleven piston cylinders are coupled to the sampling manifold to collect exhaust gas samples at eleven different depressurization pressures ≥100 psig and two evacuated canisters are coupled to the sampling manifold to collect exhaust gas samples at pressures <40 psig.

In one or more embodiments, an apparatus to characterize emissions during pig receiver depressurization includes one or more of: a sampling line configured to be fluidly coupled to an exhaust gas line positioned to accept exhaust gas released from a pig receiver such that the exhaust line extends downstream from the pig receiver, a sampling manifold positioned downstream from and in fluid communication with the sampling line, a plurality of piston cylinders coupled sequentially along the sampling manifold through piston cylinder inlet lines and positioned to collect exhaust gas samples of exhaust gas over a first range of pressures flowing through the sampling manifold, a piston cylinder inlet valve disposed in each piston cylinder inlet line positioned between each of the plurality of piston cylinders and the sampling manifold and actuated to an open position when collecting exhaust gas therethrough, a plurality of double-ended sampling cylinders coupled to the sampling manifold downstream of the piston cylinders through double-ended sampling cylinder inlet lines and positioned to collect exhaust gas samples of exhaust gas flowing through the sampling manifold at a second range of pressures lower than the first range of pressures, a double-ended sampling cylinder inlet valve disposed in each double-ended sampling cylinder inlet line between each of the plurality of double-ended cylinders and the sampling manifold and actuated to an open position when collecting exhaust gas therethrough, and a controller configured to sequentially open and close each piston cylinder inlet valve and each double-ended sampling cylinder inlet valve in response to pre-selected exhaust gas pressures during pig receiver depressurization.

Further, a control valve may be disposed in a sampling exhaust line in fluid communication with the sampling manifold and downstream thereof to control exhaust gas flow through the sampling manifold, e.g., the exhaust gas flow through the sampling manifold may be controlled to be less than the exhaust gas flow through the exhaust gas line. The control valve may be responsive to a flow meter that is disposed in the sampling exhaust line between the sampling manifold and the control valve. In one embodiment, seven piston cylinders are coupled to the sampling manifold to collect exhaust gas samples at seven different depressurization pressures ≥200 psig and five double-ended cylinders are coupled to the sampling manifold to collect exhaust gas samples at pressures <100 psig.

BRIEF DESCRIPTION OF DRAWINGS

The foregoing aspects, features, and advantages of the various embodiments will be further appreciated when considered with reference to the following detailed description and accompanying drawings. In describing the embodiments illustrated in the appended drawings, specific terminology will be used for the sake of clarity. However, these embodiments are not intended to be limited to the specific terms used, and it is to be understood that each specific term includes equivalents that operate in a similar manner to accomplish a similar purpose. In discussing various embodiments, reference may be made to the following figures:

FIGS. 8-11 present tabular data of GPA and ASTMc lab analyses for alkanes, inert gases, and BTEX for two exemplary tests involving one or more embodiments disclosed herein;

FIGS. 47-54 present tabular data of the GPA and ASTMc model fitting parameters and correlation coefficients for alkane, inert gas, and BTEX for two exemplary tests involving one or more embodiments disclosed herein;

FIG. 55 presents the inputs and outputs for the equation of state Real Gas Law models used to determine the upper limit estimate of total potential depressurization emissions;

FIG. 56 present the measured and upper limit emissions estimates using the GPA and ASTMc lab analyses as well as the Real Gas Law for two exemplary tests involving one or more embodiments disclosed herein;

FIG. 57 presents total VOC and total mass emissions with uncertainties based on VOC concentrations determined using both the GPA and ASTMc methods;

FIG. 58 presents the Ideal Gas Law estimate of VOC and total gas in the pig receiver after depressurization.

DETAILED DESCRIPTION

There is a need for systems, methods, and apparatuses to determine air emissions that are associated with the depressurization of pig receivers (and/or launchers). Various embodiments disclosed herein characterize the emissions that occur during the depressurization of natural gas pipeline pig receivers (and/or launchers). Some of these emissions can include methane ($CH_4$), ethane ($C_2H_6$), higher alkanes ($C_3$-$C_9$+), select volatile organic compounds (VOCs), and select hazardous air pollutants (HAPs), such as benzene, ethylbenzene, toluene, and xylenes. Other compounds can also be measured using one or more embodiments.

Depressurization Exhaust Gas Sampling System

Figure 1:
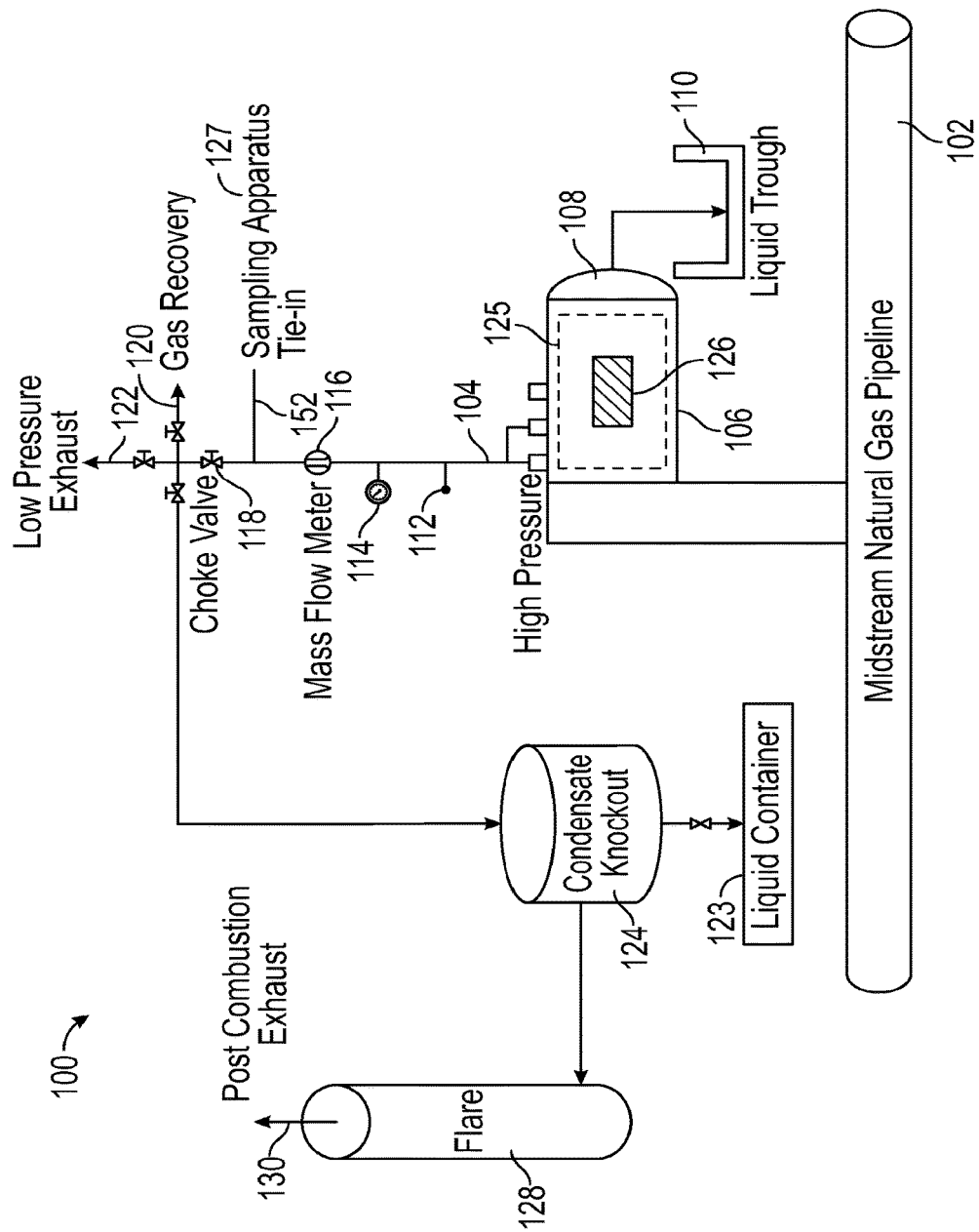
FIG. 1 is a schematic diagram of an embodiment of a pig receiver site configuration.

FIG. 1 illustrates a schematic diagram of an exemplary pig receiver site configuration 100 where a depressurization exhaust gas sampling system can be implemented in one or more embodiments, as further described below. FIG. 1 illustrates a pig receiver 106 coupled to a natural gas pipeline 102. Pig receiver 106 has a receiver barrel 125 into which pig 126 is received from the natural gas pipeline 102. Pig receiver depressurization occurs after the pig 126 is received in the pig receiver 106 and the pressurized natural gas flow between the natural gas pipeline 102 and has been isolated via one or more valves (not shown). One or more choke valves 118, in fluid communication with exhaust gas line 104, can control the flow of pressurized gas from the pig receiver 106 (as depressurization exhaust gas) into and through exhaust gas line 104, which is in fluid communication with the pig receiver 106. As shown in FIG. 1, choke valve 118 is disposed in the exhaust gas line 104 downstream of pig receiver 106. The exhaust gas flows through exhaust gas line 104 to vents at different locations. For example, exhaust gas can be: sent through gas recovery line 120 for gas recovery operations; sent to a condensate knockout drum 124 to separate out any condensed liquids into liquid container 123 and then directed to a flare 128, where the exhaust gas is combusted and the post-combustion exhaust gas is emitted through vent 130; or emitted directly to atmosphere through vent 122 (e.g., for low pressured exhaust gas). The pig receiver 106 also includes a receiver hatch 108, which can be opened after the depressurization is complete to provide access to the receiver barrel 125 of pig receiver 106 (e.g., to retrieve the pig 126) and to release any liquids into a liquid trough or container 110.

Figure 2:
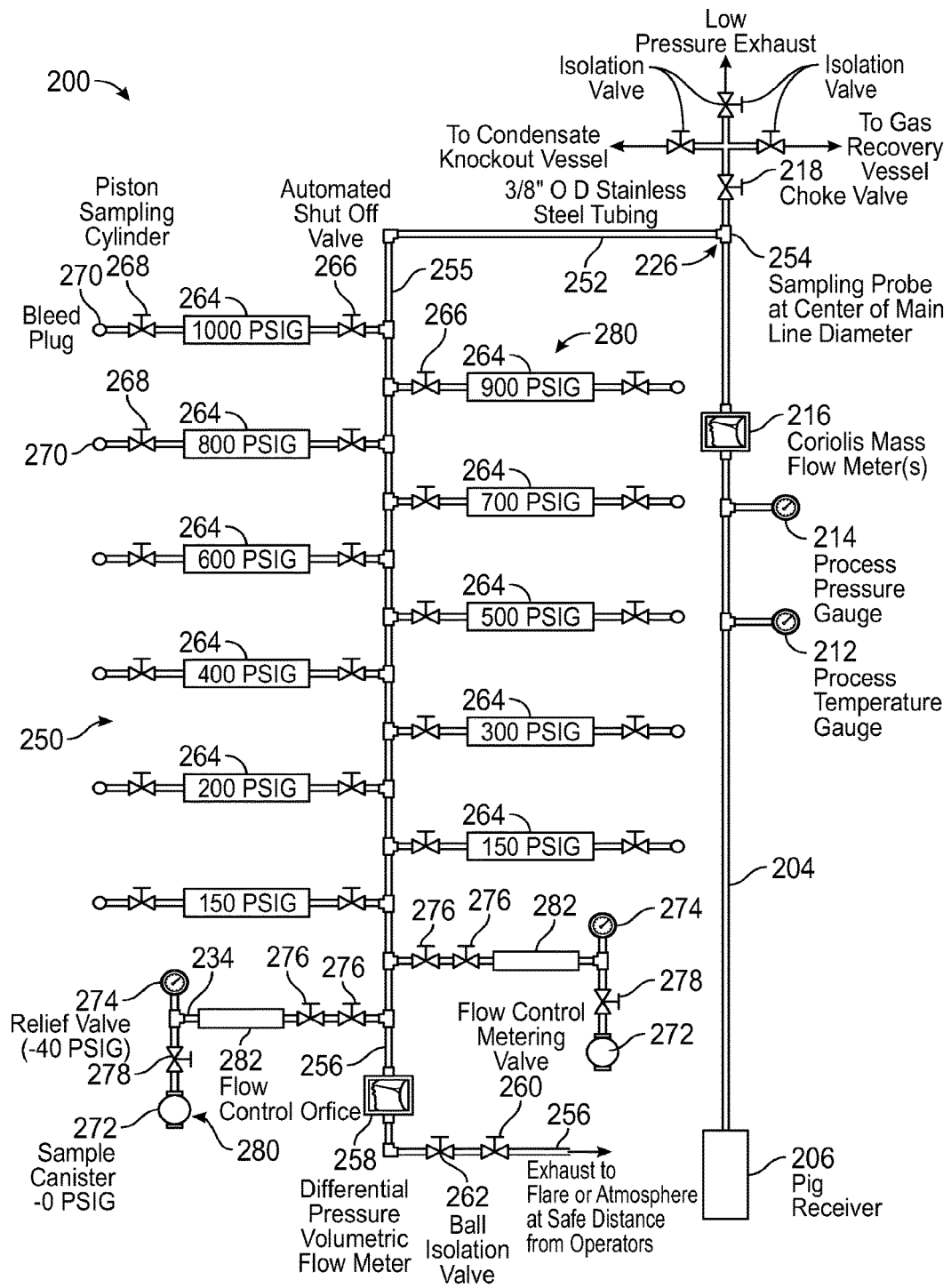
FIG. 2 is a schematic diagram of an embodiment of a system for collecting samples during pig receiver depressurization.
Figure 3:
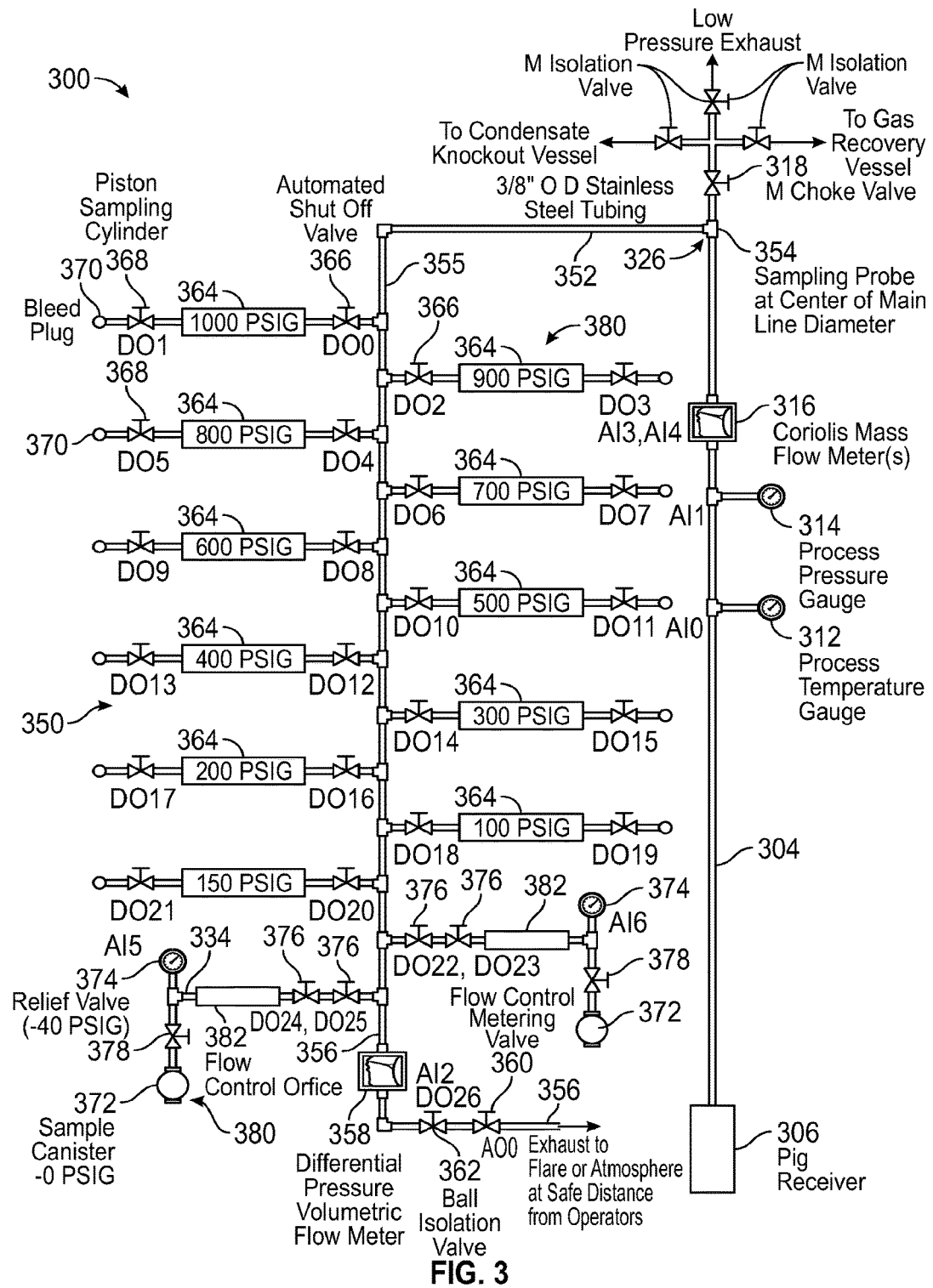
FIG. 3 is a schematic diagram of an embodiment of a system for collecting samples, illustrating digital and analog inputs and outputs.
Figure 4:
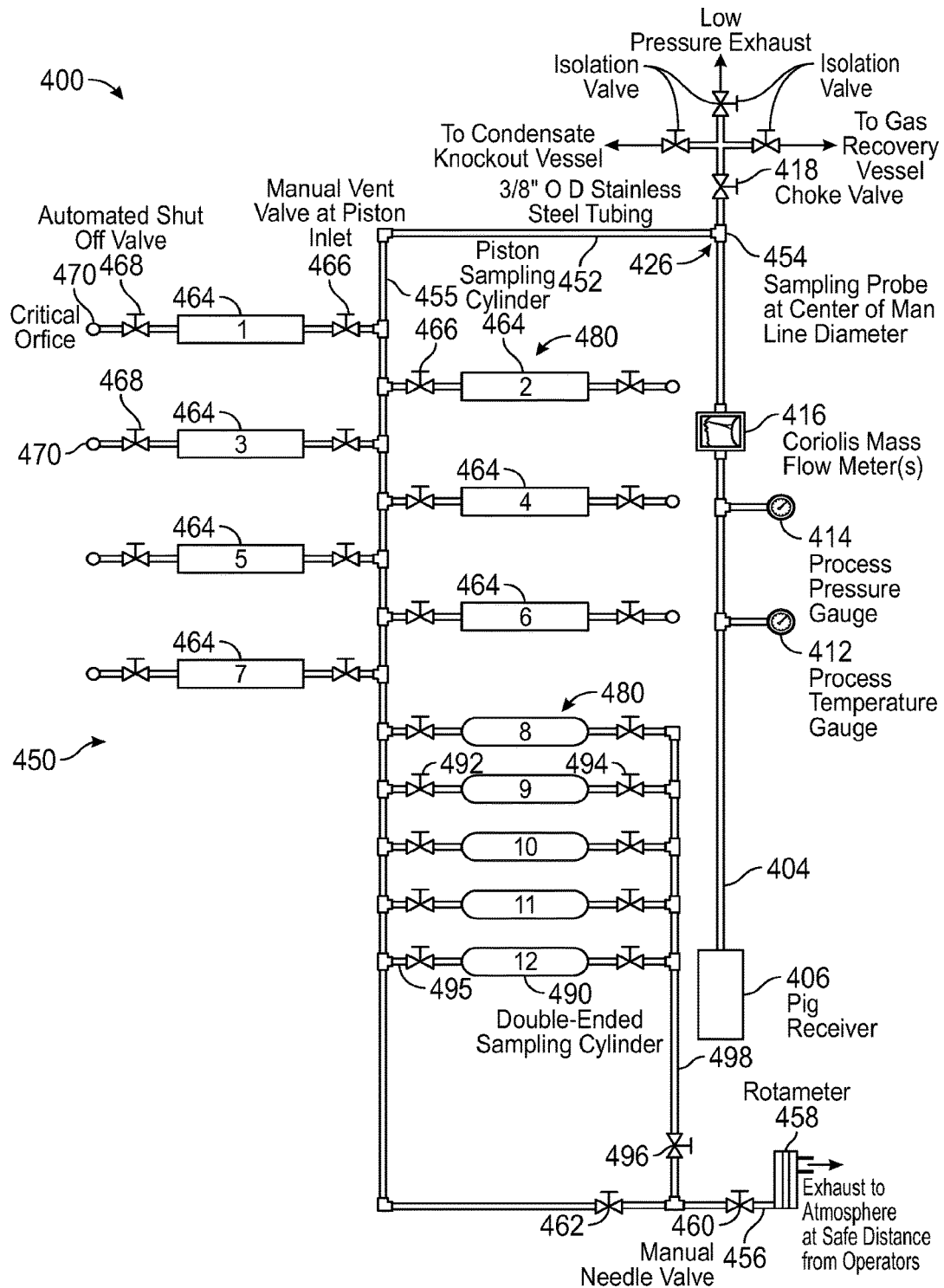
FIG. 4 is a schematic diagram of another embodiment of a system for collecting samples during pig receiver depressurization.

In one or more embodiments, the mass flow rate of the depressurization exhaust gas flowing through exhaust gas line 104 is ascertained (e.g., by measuring) as pressurized gas is released from the pig receiver and the pressure is reduced in the pig receiver 106. The total time required for pig receiver depressurization (i.e., the total time elapsed from when pressurized gas is first released from the pig receiver 106 to when pig receiver depressurization is completed) is also measured. These measurements, in addition to other measurements, allow the total mass of the pressurized gas vented from the pig receiver 106 (i.e., depressurization exhaust gas), which subsequently flows through exhaust gas line 104, to be calculated. Depressurization exhaust gas flow rate measurements can be made using a Coriolis mass flow meter 116, which is disposed in exhaust gas line 104. One or more in-line pressure sensors or gauges 114 and temperature sensors or gauges 112, also disposed in exhaust gas line 104, can manually or automatically ascertain (e.g., by measuring) and record pressure and/or temperature, respectively, during the total time or elapsed time of pig receiver depressurization. A slip stream sampling apparatus tie-in location 127 is shown in FIG. 1, where an embodiment of the slip stream sampling apparatus (see FIGS. 2-4 showing that portion of the depressurization exhaust gas sampling system positioned downstream of the slip stream 152 at tie-in location 127) may be integrated into the exemplary pig receiver site configuration of FIG. 1. As described in greater detail below, the slip stream sampling apparatus includes a grab sample collection train having one or more grab sample containers as well as one or more flow meters and flow control valves downstream thereof to control the flow of exhaust gas through the slip stream/sampling line. In one or more embodiments, the depressurization exhaust gas sampling system (see FIGS. 2-4) includes the exhaust gas line 104, mass flow meter 116, pressure and temperature sensors 112, 114, control valve 118, and the slip stream sampling apparatus.

FIGS. 2, 3, and 4 illustrate exemplary piping and instrumentation diagrams of the depressurization exhaust gas sampling system 200, 300, 400 according to various embodiments. For convenience, analogous components of FIGS. 2, 3, and 4 will be discussed in conjunction with each other. Components of the depressurization exhaust gas sampling system 200, 300, 400 include a grab sample collection train 250, 350, 450 that is preceded by a mass flow meter 216, 316, 416, pressure sensors/gauges 214, 314, 414, and temperature sensors/gauges 212, 312, 412, disposed in exhaust gas line 204, 304, 404. FIGS. 2-4 also depict the temperature sensors, pressure sensors, and mass flow meter shown in FIG. 1 as these elements are part of depressurization sampling system 200, 300, 400. As shown in FIGS. 2-4, slip stream or sampling line 252, 352, 452 is coupled to and in fluid communication with the exhaust gas line 204, 304, 404 upstream of the depressurization control or choke valve 218, 318, 418 and downstream of pig receiver 206, 306, 406 as well as temperature 212, 312, 412 sensors and pressure sensors 214, 314, 414.

A direct read Coriolis mass flow meter 216, 316, 416 can be used to measure the mass flow rate of exhaust gas flowing through exhaust gas line 204, 304, 404. One or more additional Coriolis mass flow meters can be added in series if the range of a single meter does not cover the entire range of mass flow rates expected during depressurization or if the accuracy of the overall mass flow is significantly impacted. As shown, exhaust temperature gauge or sensor 212, 312, 412 and exhaust pressure gauge or sensor 214, 314, 414 can also be disposed within the exhaust gas line 204, 304, 404. The temperature and pressure ascertained from these above-described sensors can be used, e.g., to compensate for the Coriolis meter tube stiffness, to calculate the mass flow of gas components released from pig receiver 206, 306, 406 during depressurization, and to correct for sampling time delay.

A sampling probe 254, 354, 454 can be disposed at the depressurization sampling tie-in 226, 326, 426 to the exhaust gas line 204, 304, 404 in order to supply or direct a slip stream/sampling line 252, 352, 452 containing the exhaust gas to the sampling manifold 255, 355, 455 of grab sample collection train 250, 350, 450. For example, the tip of the sample probe 254, 354, 454 can be inserted into the middle third of the cross-section of the exhaust gas line 204, 304, 404. As such, the slip stream/sampling line 252, 352, 452 is in fluid communication with the exhaust gas line 204, 304, 404 originating from pig receiver 206, 306, 406. Further, slip stream/sampling line 252, 352, 452 is coupled to and in fluid communication with the sampling manifold 255, 355, 455 of grab sample collection train 250, 350, 450.

The grab sample collection train 250, 350, 450 includes the sampling manifold 255, 355, 455, which has a plurality of grab sample containers 280, 380, 480 coupled, e.g., sequentially, therealong and is selectively in fluid communication therewith. A grab sample container is selectively positioned to be in fluid communication with the sampling manifold 255, 355, 455 when a grab sample (i.e., exhaust gas sample) is to be collected. In one or more embodiments, the grab sample containers 280, 380, 480 of the grab sample collection train 250, 350, 450 can be used to collect grab samples (i.e., exhaust gas samples) in a staged manner at predetermined or preselected exhaust pressure values during the depressurization of pig receiver 206, 306, 406. In one or more other embodiments, the grab sample containers 280, 380, 480 of the grab sample collection train 250, 350, 450 can be used to collect grab samples (i.e., exhaust gas samples) in a staged manner at desired times during the depressurization of the pig receiver 206, 306, 406.

The exhaust gas, which was released from pig receiver 206, 306, 406, passed through exhaust gas line 204, 304, 404 and was directed into slip stream/sampling line 252, 352, 452, is continuously passed into and through the sampling manifold 255, 355, 455 of the grab sample collection train 250, 350, 450 and into and through the sampling exhaust line 256, 356, 456, which exhausts to a flare or to the atmosphere at a safe distance from operators. Thus, a sampling flow path of the exhaust gas through the depressurization exhaust gas sampling system 200, 300, 400 is defined by the exhaust gas line 204, 304, 404, the slip stream/sampling line 252, 352, 352, the sampling manifold 255, 355, 455 of the grab sample collection train 250, 350, 450, and the sampling exhaust line 256, 356, 456, which permit fluid communication therethrough from the pig receiver 206, 306, 406.

Measurements from a flow meter 258, 358, 458 disposed in the sampling exhaust line 256, 356, 456, are used to control a flow control valve 260, 360, 460, positioned downstream thereof. The flow meters 258, 358 of FIGS. 2 and 3 are depicted as differential pressure volumetric flow meters and the flow meter 458 of FIG. 4 is depicted as a rotameter, however, such flow meters may be interchanged in one or more embodiments. Further, the flow control valves 260, 360 of FIGS. 2 and 3 are depicted as automatic flow control metering valves and the flow control valve 460 of FIG. 4 is depicted as a manual needle valve, however, such flow control valves may be interchanged in one or more embodiments. The flow of exhaust gas through sampling exhaust line 256, 356, 456 is controlled by flow control valve 260, 360, 460 in order to allow a controlled amount of exhaust gas (e.g., <50 SLPM) to be exhausted to flare or atmosphere while providing a continuous flow of exhaust gas to the grab sample collection train 250, 350, 450 for sampling. In one or more embodiments, the exhaust gas flow through the sampling manifold 255, 355, 455 is controlled by flow control valve 260, 360, 460 to be less than the exhaust gas flow through the exhaust gas line 204, 304, 404. The largest pressure drop of the sampling collection train 250, 350, 450 occurs across the flow control valve 260, 360, 460. The pressure of the exhaust gas in the slip stream/ sampling line 252, 352, 452, in the sampling manifold 255, 355, 455 and that portion of the sampling exhaust line 256, 356, 456 upstream of the flow control valve 260, 360, 460 is approximately that of the pig receiver, 206, 306, 406, while downstream thereof the exhaust gas pressure is approximately atmospheric pressure.

When the desired or preselected pressure is reached during the depressurization of pig receiver 206, 306, 406, for example as measured by pressure sensor 214, 314, 414, an inlet valve 266, 366, 466, 282, 383 disposed in the inlet line between the sampling manifold 255, 355, 455 and one of the grab sample containers 280, 380, 480 (e.g., a piston cylinder or evacuated canister as described below) is actuated such that the one of the grab sample container 280, 380, 480 obtains a grab sample or exhaust gas sample of the exhaust gas associated with that desired or preselected pressure. When the next desired or preselected pressure is reached during the depressurization of pig receiver 206, 306, 406, an inlet valve 266, 366, 466, 282, 382 disposed in the inlet line between the sampling manifold 255, 355, 455 and another one of the grab sample containers is actuated such that the another one of the grab sample containers obtains a grab sample or exhaust gas sample of the exhaust gas associated with that desired or preselected pressure. Valves disposed in the inlet lines between the sampling manifold 255, 355, 455 and the grab sample containers 280, 380, 480 are thus sequentially actuated in order to obtain grab samples associated with desired or preselected exhaust gas pressures. Thus, the exhaust gas samples are collected in a staged manner. One or more isolation valves 262, 362, 462 can be used along with the flow control valve 260, 360, 460 to regulate the flow of exhaust gas through slip stream/sampling line 252, 352, 452, sampling manifold 255, 355, 455 and sampling exhaust line 256, 356, 456.

In one or more embodiments (see, e.g., FIGS. 2-4 and accompanying text), the sample collection train 250, 350, 450 has grab sample containers 280, 380, 480 that include a plurality of piston cylinders 264, 364, 464 that are used to obtain or collect samples of exhaust gas at different pressures from the sampling manifold 255, 355, 455. As shown in FIG. 2, e.g., the piston cylinder 264 at the upper left of the sample collection train 250 is depicted as being designated for the 1,000 psig exhaust gas sample. The piston cylinders 264 in the remaining portion of the sample collection train therebelow are each depicted as being designated for lesser pressure exhaust gas samples, e.g., from 900 psig to 150 psig. The piston cylinders 364, 464 illustrated in FIGS. 3 and 4 are similarly configured.

Figure 5:
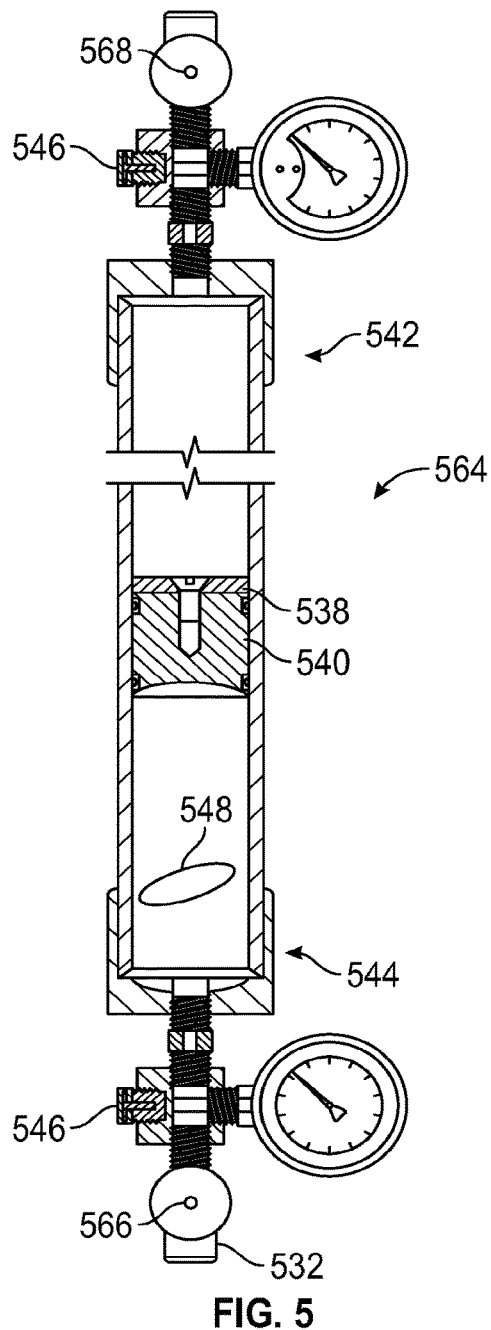
FIG. 5 is a schematic sectional view of an embodiment of a sampling piston cylinder.

A schematic of a Welker CP2 piston cylinder is provided in FIG. 5 as an example of a piston cylinder 564. These high pressure piston cylinders 564 can be initially back-pressured to the desired sampling pressure with an inert gas on an inert gas or outlet side 542 of the cylinder (e.g., 1,000 psig with Helium). High pressure piston cylinders 564 can be rated to ≥1,800 psig and include burst discs 546 to safely relieve pressure if the pressure rating is exceeded. A mag ring 538 can be positioned above (i.e., on the inert gas side 542 of) piston 540 so that an external indicator shows the position of the piston 540 within the piston cylinder 564. The sampling piston cylinder 564 can include an ellipsoid mixer 548 in the piston chamber 536 on the exhaust gas side of piston cylinder 564. A piston cylinder inlet valve 566 can allow gases to enter the piston chamber 536 via a piston cylinder inlet line 532, which pushes piston 540 to pressure the release of the inert gas on the inert gas side 542 of piston 540 via inert gas or outlet valve 568. The sampling piston cylinder 564 can further include a pre-charge or outlet valve 568.

Returning to FIGS. 2-4, to obtain a grab sample or exhaust gas sample of exhaust gas using a piston cylinder 264, 364, 464, an inlet valve 266, 366, 466 of the piston cylinder 264, 364, 464 is opened that allows the exhaust gas in the sampling manifold 255, 355, 455 to fill the inlet side of the piston cylinder 264, 364, 464. An outlet valve 268, 368, 468 of the piston cylinder 264, 364, 464 is simultaneously opened to exhaust an inert gas, e.g., nitrogen, helium, etc., on the outlet side of the piston cylinder 264, 364, 464 and to thus obtain a grab sample of the exhaust gas from sampling manifold 255, 355, 455 on the inlet side at the desired or preselected pressure. A critical orifice 270, 370, 470 can be installed on the outlet side of the piston cylinder 264, 364, 464 to control the rate at which the grab sample/exhaust gas sample is obtained. The sample or inlet side valves 266, 366, 466 and inert gas or outlet side valves 268, 368, 468 are automatically closed after the sample is obtained; however, in one or more embodiments these valves may be manually closed after the sample is obtained.

In one or more embodiments (see, e.g., FIGS. 2-3 and accompanying text), the sample collection train 250, 350 has grab sample containers 280, 380, 480 that include a plurality of evacuated canisters 272, 372 (e.g., SUMMA canisters) that are used to obtain or collect samples of exhaust gas at different pressures, e.g., less than 10 psig, near or at ambient pressure, etc., from the sampling manifold 255, 355. Evacuated canisters 272, 372 are depicted in FIGS. 2 and 3 as passivated, evacuated canisters (i.e., at a vacuum). To obtain a grab sample or exhaust gas sample of ambient or near ambient pressure from sampling manifold 255, 355, an evacuated canister inlet valve or flow control orifice 282, 382 is opened to allow the evacuated canister 272, 372 to fill with a sample of exhaust gas from sampling manifold 255, 355 via evacuated canister inlet line 234, 334 until ambient pressure is reached as measured with a pressure sensor or gauge 274, 374. Once the evacuated canister is filled, then the evacuated canister inlet valve 282, 382 is automatically closed. In one or more embodiments, each evacuated canister 272, 372 is a portion of an assembly that includes evacuated canister 272, 372 preceded by two pneumatic ball valves 276, 376, vacuum pressure gauge 274, 374, pressure relief valve 278, 378, a flow control orifice 282, 382, and a manual three way valve (not shown). The duplicity of pneumatic valves 276, 376 reduces or eliminates overpressurization in the event a single valve leaks. The reading from the vacuum pressure gauge 274, 374 can be used to ensure the pneumatic valves 276, 376 are closed if the grab sample canister 272, 372 reaches ambient pressure to prevent the grab sample canister 272, 372 from being overpressurized. The pressure relief valve 278, 378 can be spring loaded to automatically vent exhaust gas to atmosphere if the pressure in the evacuated canister inlet line 234, 334 between flow control orifice 282, 382 and the evacuated canister 272, 372 approaches the pressure rating of the evacuated canister 272, 372. A manual three-way valve (not shown) can be used to purge the line between the sampling manifold 255, 355 and the evacuated canister 272, 372 with helium before sampling. In one of more embodiments, the evacuated canister 272, 372 is initially evacuated to approximately negative 30" Hg and the pressure increases as a sample of exhaust gas is obtained.

FIGS. 2 and 3 depict exemplary embodiments having a sample collection train 250, 350 with eleven piston cylinders 264, 364 and two evacuated canisters 272, 372 used to collect grab samples of exhaust gas in a staged manner at predetermined or preselected pressure values. Each of the inlet lines between sampling manifold 255, 355 and the individual cylinders 264, 364 and canisters 272, 373 operate independently, such that the grab sample containers 280, 380 may be filled with exhaust gas in any desired order. When the desired sampling pressure is reached, for example, as may be determined with pressure sensors 214, 314, a valve sequence is automatically initiated to open one of piston cylinder inlet valves 266, 366 to obtain a sample using one of the piston cylinders 264, 364, as previously described. For example, exhaust gas samples can be taken sequentially at 100 psig intervals from about 1,000 psig down to about 100 psig using the eleven piston cylinders 264, 364. Samples of the lower pressure exhaust gas can then be taken using the evacuated canisters 272, 372 after the pig receiver 206, 306 has depressurized to low pressures (e.g., approaching 0 psig). Once the pig receiver 206, 306 has depressurized to low pressures, for example, as may be determined with pressure sensors 214, 314, another valve sequence is automatically initiated to open one of the two evacuated canister inlet valves 282, 382 to obtain a sample using one of the two evacuated canisters 272, 372. Finally, the remaining canister 272, 373 may be used to sample the exhaust gas at less than 10 psig to near 0 psig. While eleven piston cylinders 264, 364 and two evacuated canisters 272, 373 are depicted on FIGS. 2 and 3, any number of grab sample containers 280, 380 can be used to obtain exhaust gas from pig receiver 206, 306 via sampling manifold 255, 355 at any pressure during depressurization to best characterize the depressurization process.

In one or more embodiments (see, e.g., FIG. 4 and accompanying text), the sample collection train 450 has grab sample containers 480 that include a plurality of double-ended sampling cylinders 490 that are used to obtain or collect samples of exhaust gas at different pressures from the sampling manifold 455. The double-ended sampling cylinders 490 obtain samples over four steps. First, referring to FIG. 4, the double-ended cylinder inlet valve 492 is opened (e.g., for approximately two seconds) while the double-ended cylinder outlet valve 494 is closed to allow exhaust gas from the pig receiver 406 via sampling manifold 455 and double-ended cylinder inlet line 495 to mix with helium in the double-ended sampling cylinder 490 and for the mixed gas in the cylinder 490 to equilibrate to the pressure of the sampling manifold 455. During this time, the sampling line exhaust valve 462 is closed while the double-ended cylinder manifold exhaust valve 496 is opened to release any pressurized gas in the manifold 498. Second, the cylinder outlet valve 494 is opened (e.g., for approximately three seconds) to purge the double-ended sampling cylinder 490 of the mixed helium and exhaust gas. Third, the cylinder outlet valve 494 is closed (e.g., for approximately three seconds) to allow the pressure of the exhaust gas flowing into the double-ended sampling cylinder 490 to reach the pressure in the sampling manifold 455. Fourth, the cylinder inlet valve 492 is closed to isolate the double-ended sampling cylinder 490, and the sampling line exhaust valve 462 is opened to purge the sampling exhaust line 456.

Figure 6:
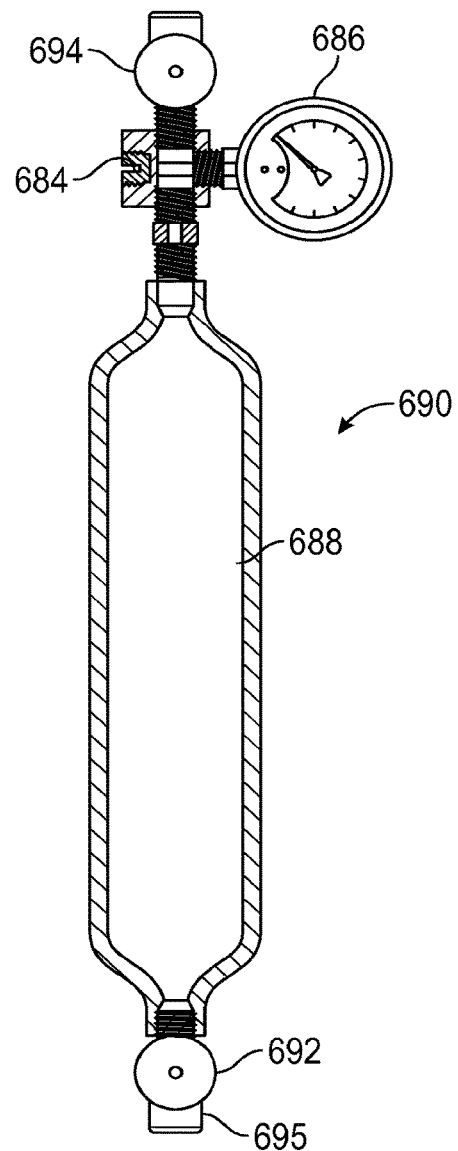
FIG. 6 is a schematic sectional view of an embodiment of a double-ended sampling cylinder.

A schematic of a double-ended sampling cylinder 690 (e.g., Swagelok) is provide in FIG. 6 as an example of a double-ended sampling cylinder 690. As shown in FIG. 6, the double-ended sampling cylinder has an inner chamber 688, an inlet valve 692, an inlet line 695, and an outlet valve 694. A pressure gauge 686 may be disposed near the outlet valve 694 to measure pressure inside inner chamber 688. A burst disc 684 may be disposed in or near the outlet valve 694 to ensure that the inner chamber 688 is not over-pressurized. As a safety measure, the burst disc 684 is designed to burst and release exhaust gas a pressure lower than the pressure at which the inner chamber 688 itself would burst.

FIG. 4 depicts an exemplary embodiment having a grab sample collection train 450 with seven piston cylinders 464 and five double-ended sampling cylinders 490 used to collect grab samples/exhaust gas samples of exhaust gas in a staged manner at predetermined or preselected pressure values. Each of the inlet lines between sampling manifold 455 and the individual piston cylinders 464 and double-ended sampling cylinders 490 operate independently, such that the grab sample containers 480 may be filled in any order. When the desired sampling pressure is reached, for example, as may be determined with pressure sensor 414, a valve sequence is automatically initiated to open one of the piston cylinder inlet valves 466 to obtain a sample using one of the piston cylinders 464, as previously described. For example, the seven piston cylinders 464 can sequentially collect samples of exhaust gas at pressure values of 1,000, 850, 700, 550, 550, 400, and 200 psig. As depicted in FIG. 4, these seven pressure values respectively correspond to the seven piston cylinders labeled 1 through 7. Samples of lower pressure exhaust gas can then be taken using the double-ended sampling cylinders 490 after the pig receiver 406 has depressurized to low pressures (e.g., from about 100 psig down to about 0 pisg). Once the pig receiver 406 has depressurized to low pressures, for example, as may be determined by pressure sensor 414, another valve sequence is automatically initiated to open one of the double-ended cylinder inlet valves 492 in conjunction with sampling steps disclosed above with respect to the double-ended sampling cylinders 490. For example, the double-ended sampling cylinders 490 can collect samples at 100, 75, 50, 10, and approximately 0 psig. As depicted in FIG. 4, these five pressure values respectively correspond to the five double-ended sample cylinders 8 through 12. While seven piston cylinders 464 and five double-ended sampling cylinders 490 are depicted in FIG. 4, any number of garb sample containers 480 can be used to obtain exhaust gas from pig receiver 406 via sampling manifold 455 at any pressure during depressurization to best characterize the depressurization process.

Each exhaust gas sample has associated therewith the exhaust pressure and temperature ascertained, e.g., from pressure sensor 214, 314, 414 and from temperature sensor 212, 312, 412, when the exhaust gas sample was obtained. Similarly, each exhaust gas sample has associated therewith the mass flow rate ascertained, e.g., from mass flow meter 218, 318, 418, when the exhaust gas sample was obtained. A sampling time period is also measured for each exhaust gas sample obtained. Further, an elapsed time for each exhaust gas sample is measured and recorded. The elapsed times are measured from when pressurized gas is first released from the pig receiver to when each of the plurality of exhaust gas samples is obtained.

Figure 7:
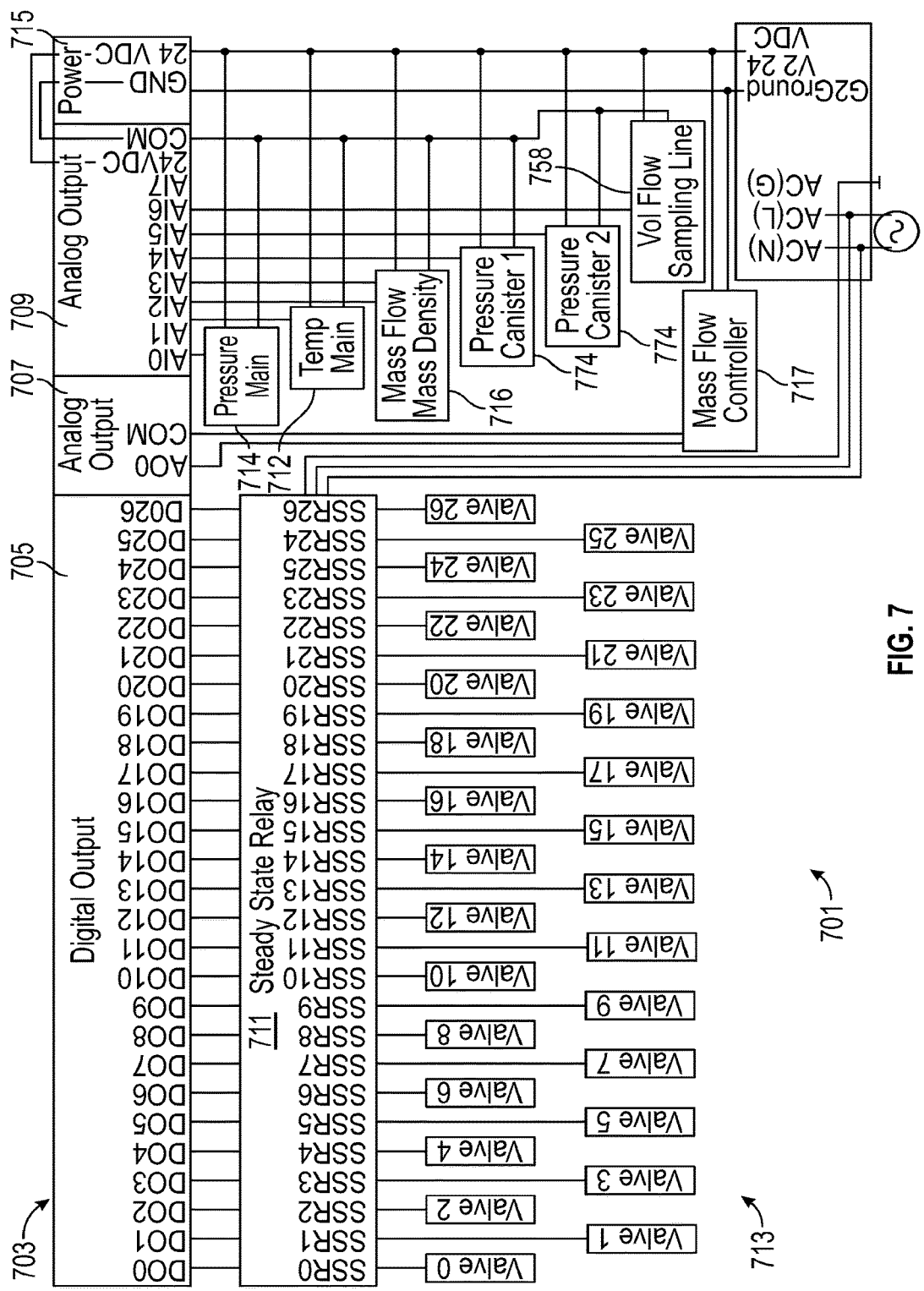
FIG. 7 is a schematic diagram of an embodiment of a data acquisition and control system.
Figure 12A:
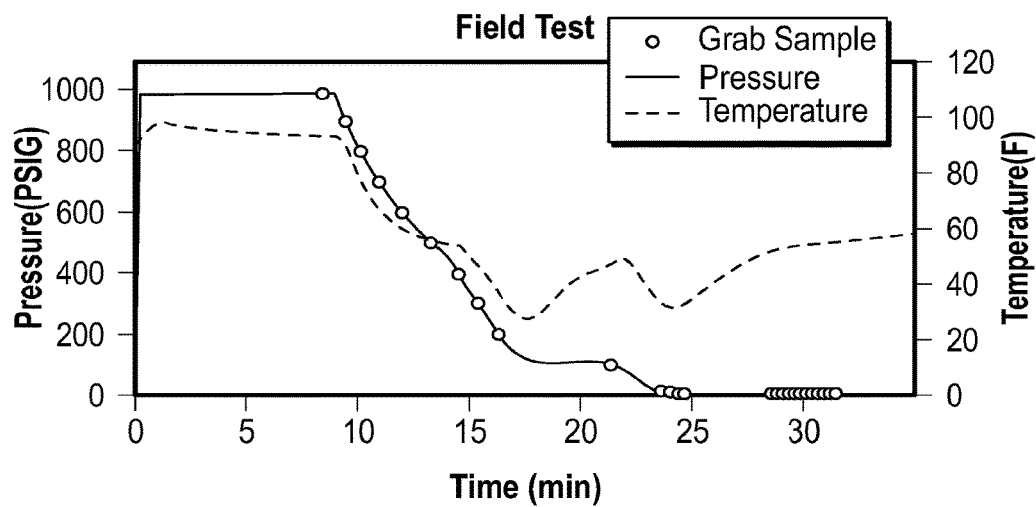
FIGS. 12A, 12B, 12C, and 12D present graphical data of pressure, temperature, mass flow rate, and cumulative mass emissions for pressurized gas vented from a pig receiver during two exemplary tests involving one or more embodiments disclosed herein.
Figure 12B:
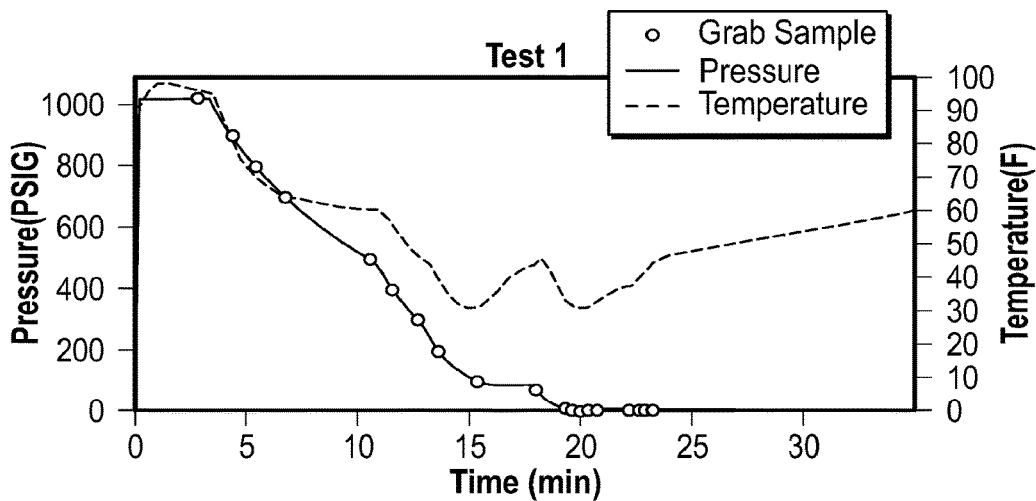
Figure 12C:
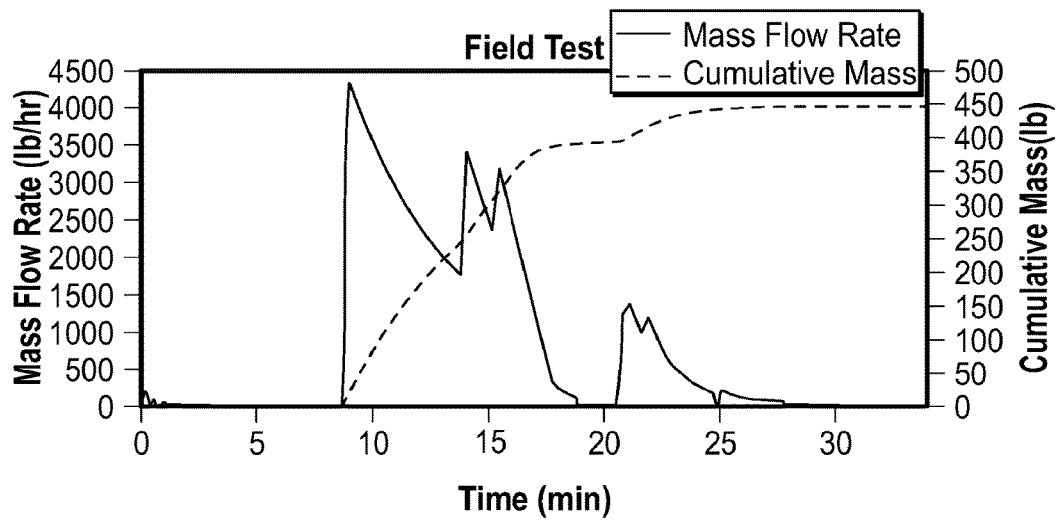
Figure 12D:
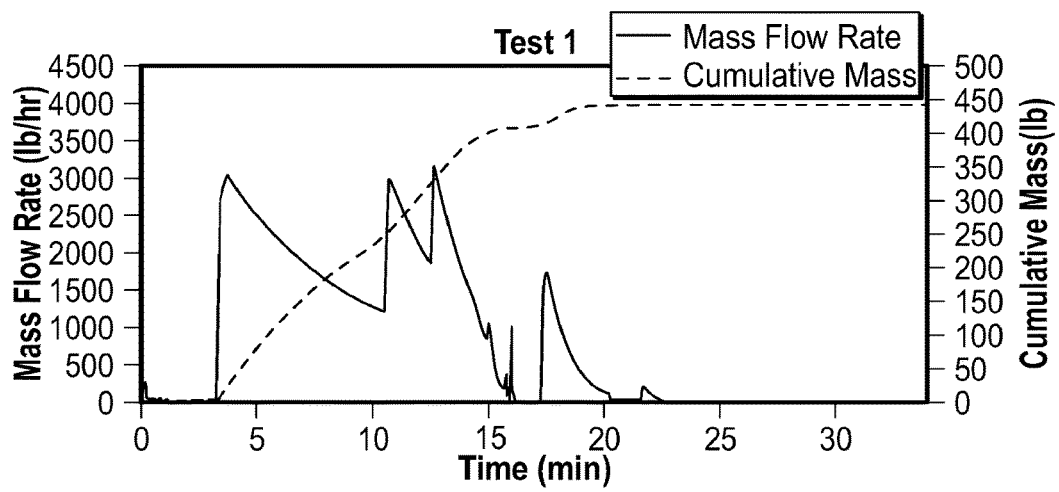
Figure 13:
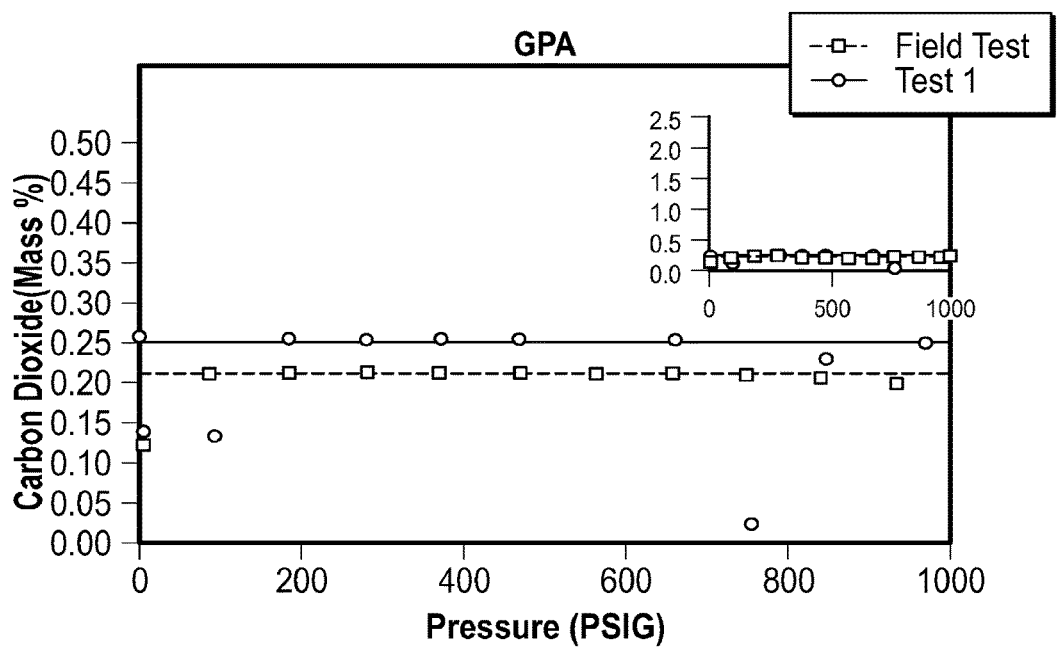
FIGS. 13-46 present graphical data of the measured mass concentrations for individual gas components from GPA and ASTMc lab analyses for two exemplary tests involving one or more embodiments disclosed herein, along with modeled mass concentrations for the depressurization pressure range.
Figure 14:
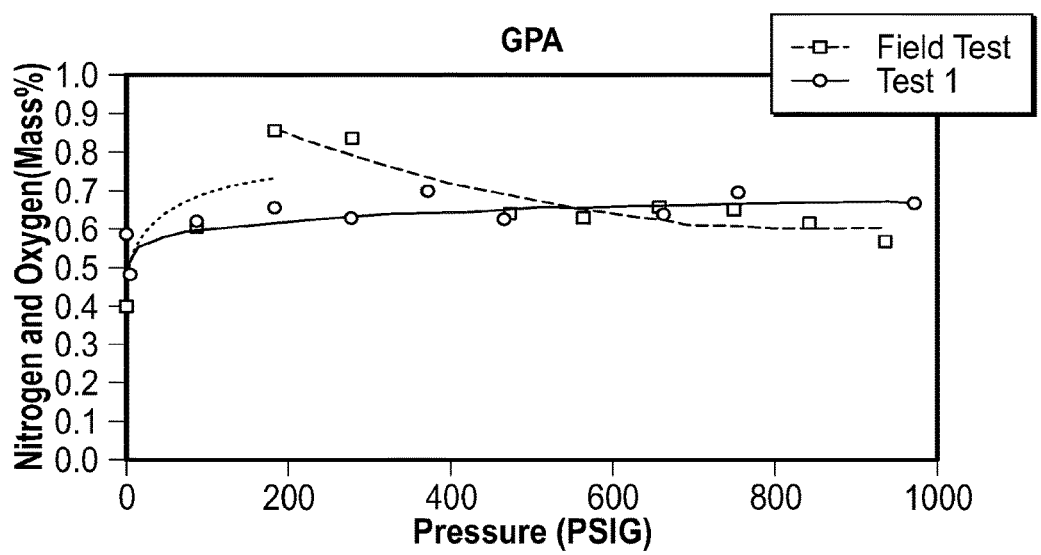
Figure 15:
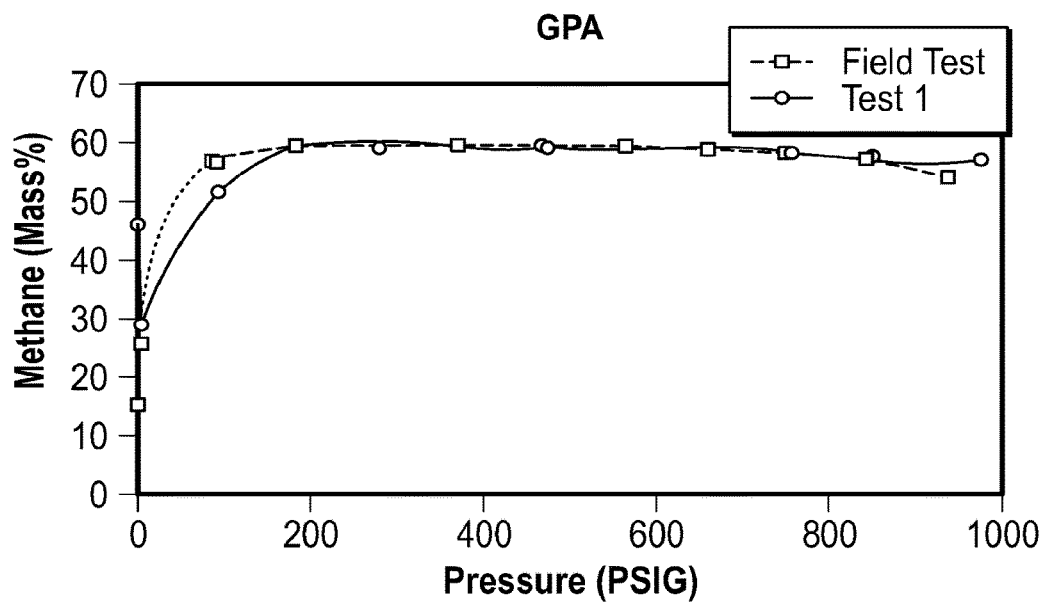
Figure 16:
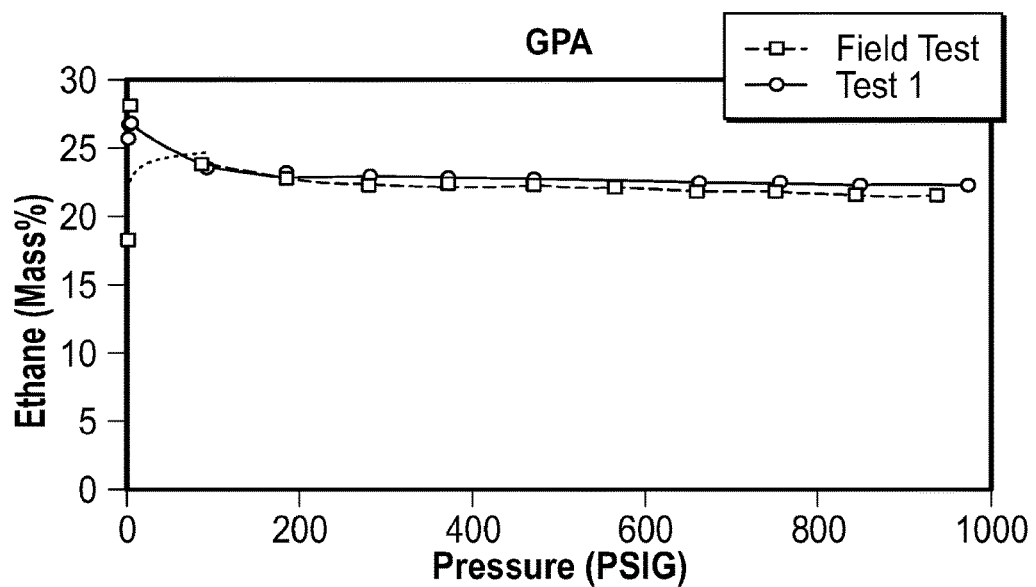
Figure 17:
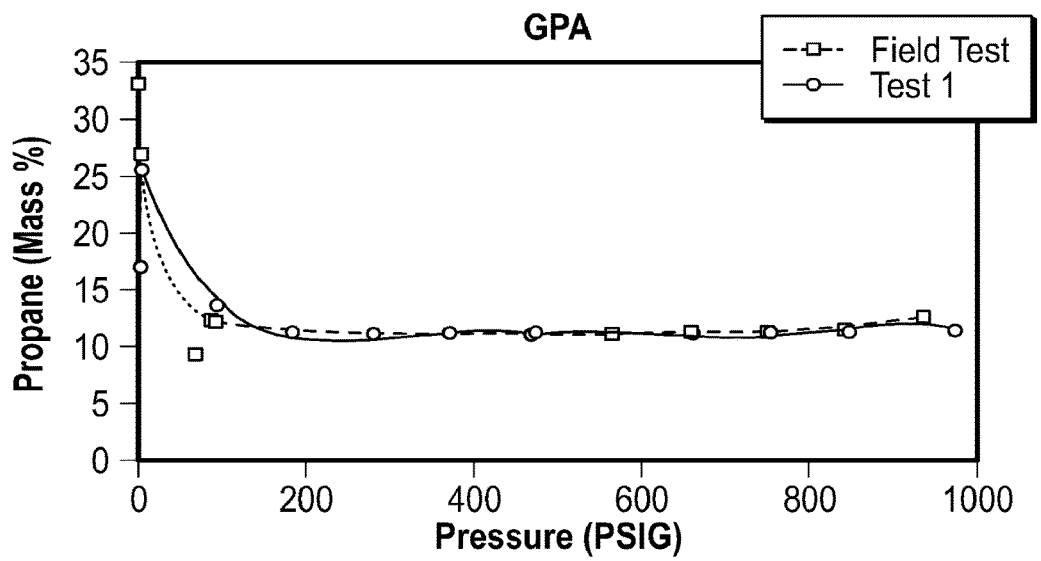
Figure 18:
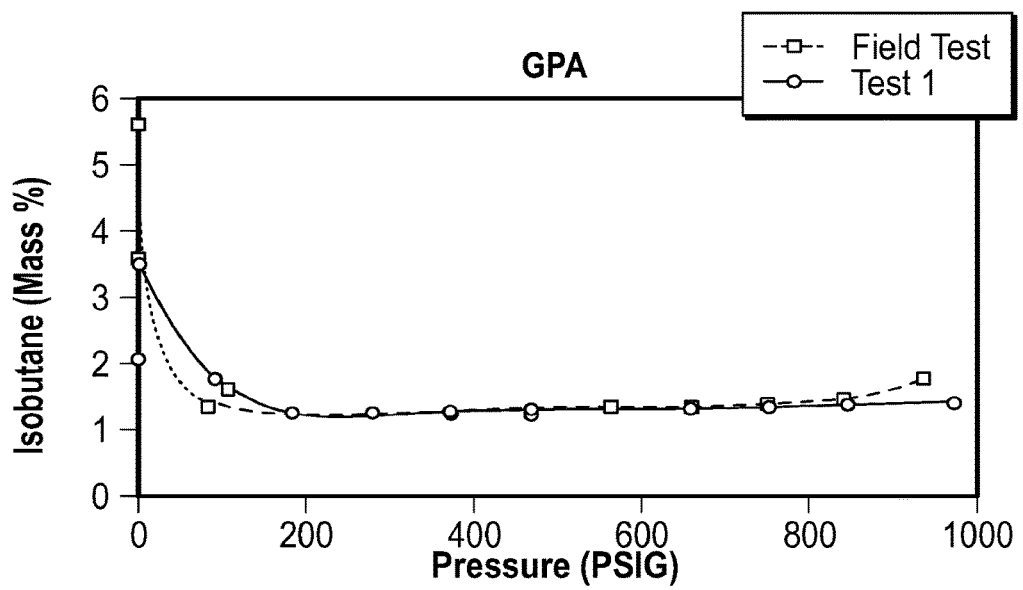
Figure 19:
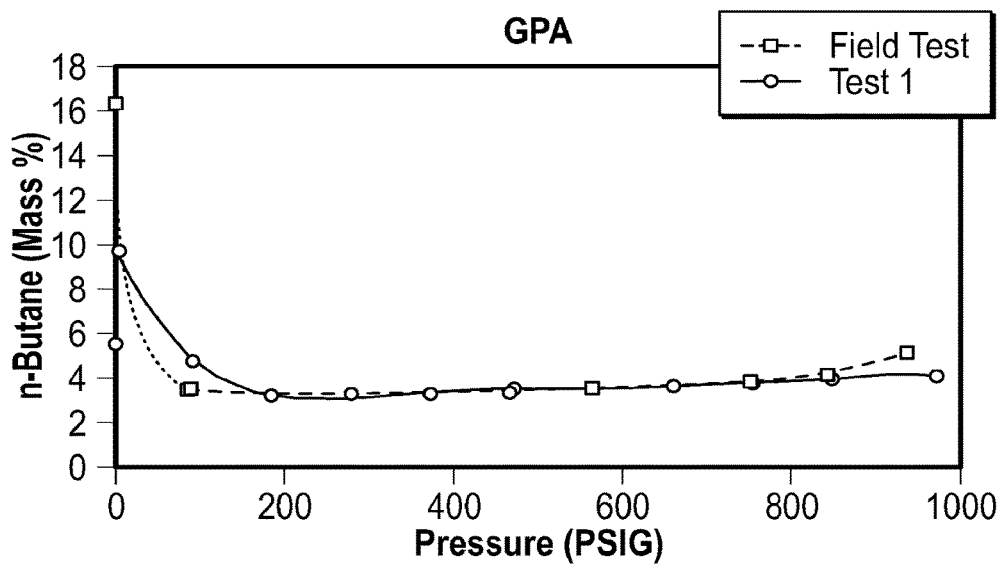
Figure 20:
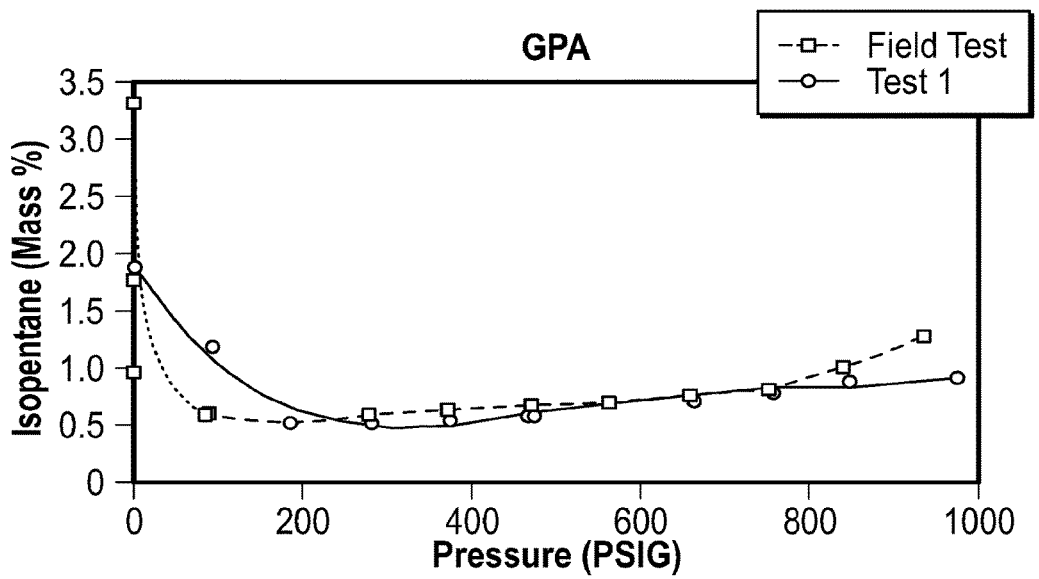
Figure 21:
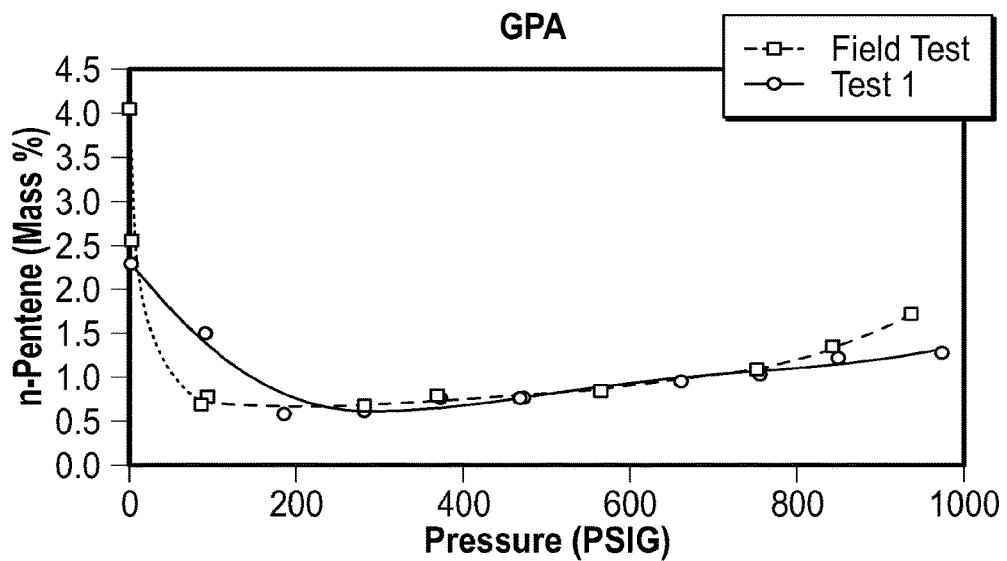
Figure 22:
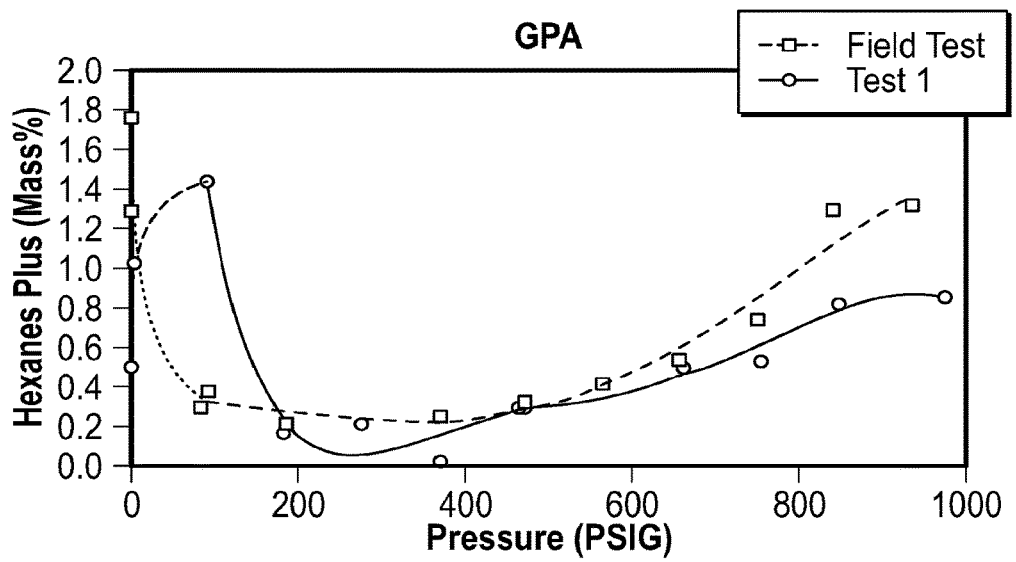
Figure 23:
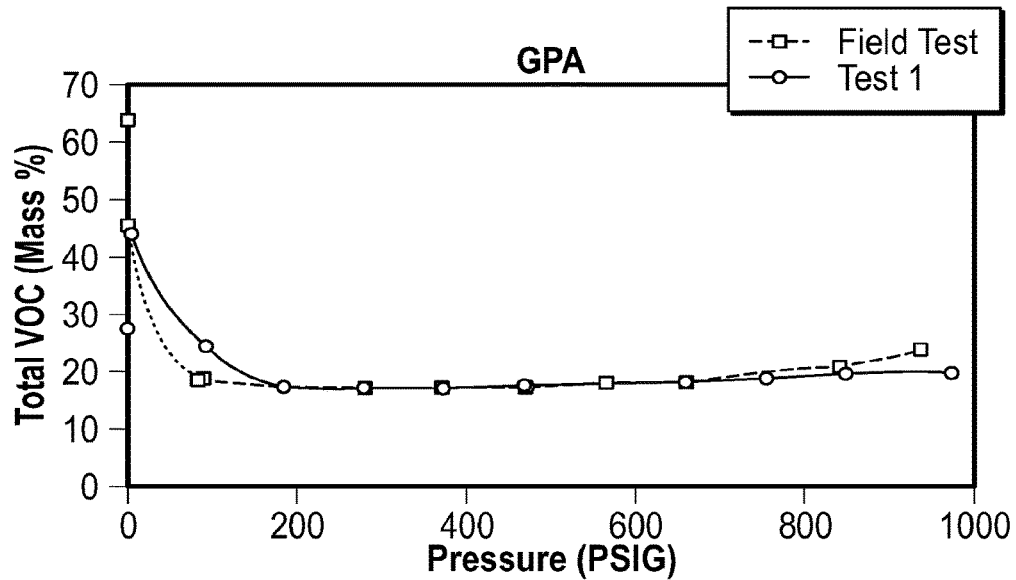
Figure 24:
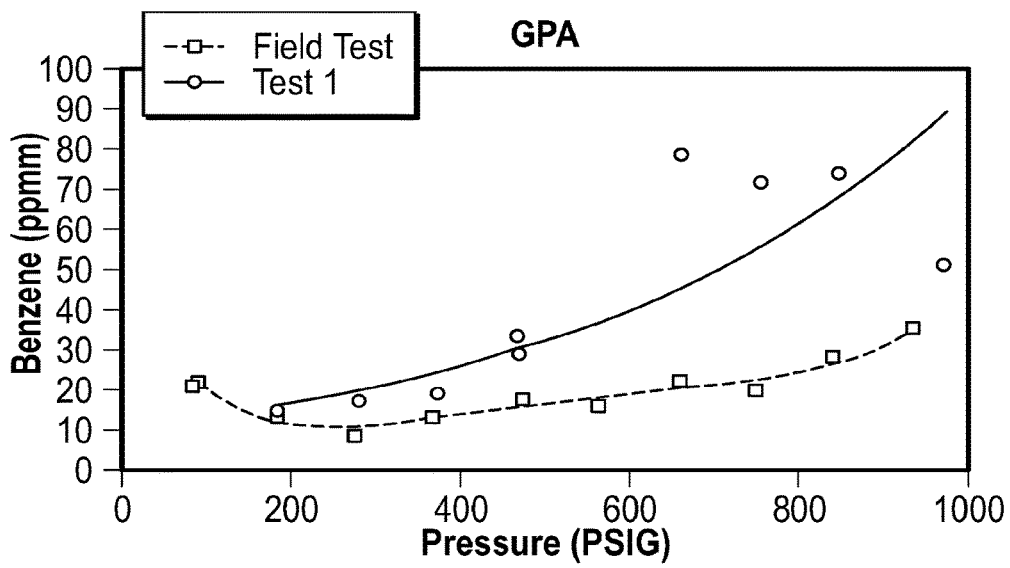
Figure 25:
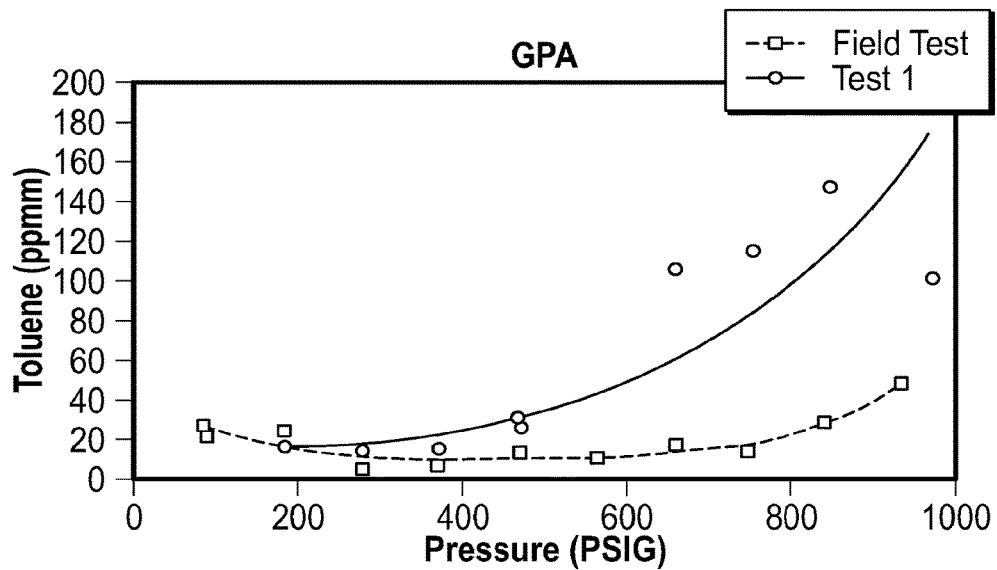
Figure 26:
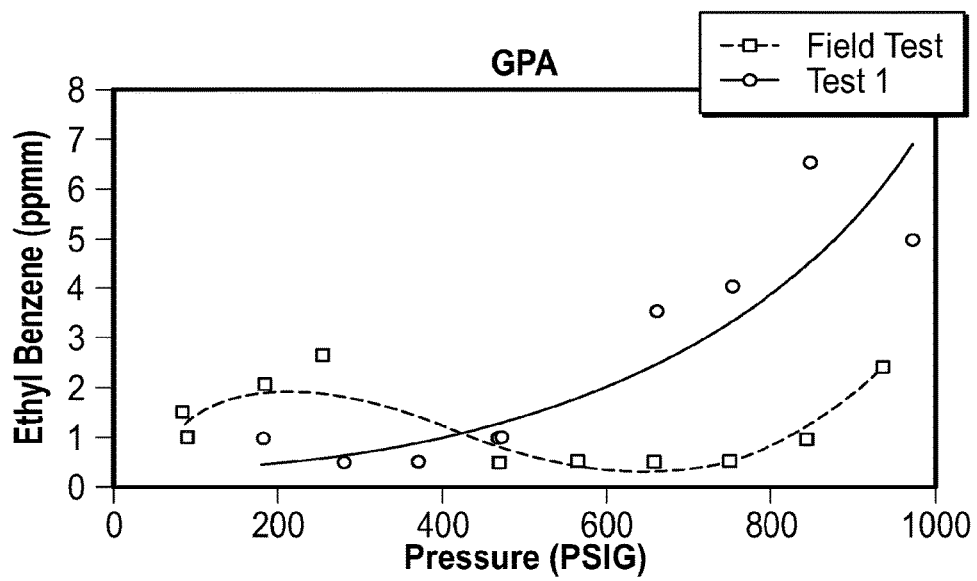
Figure 27:
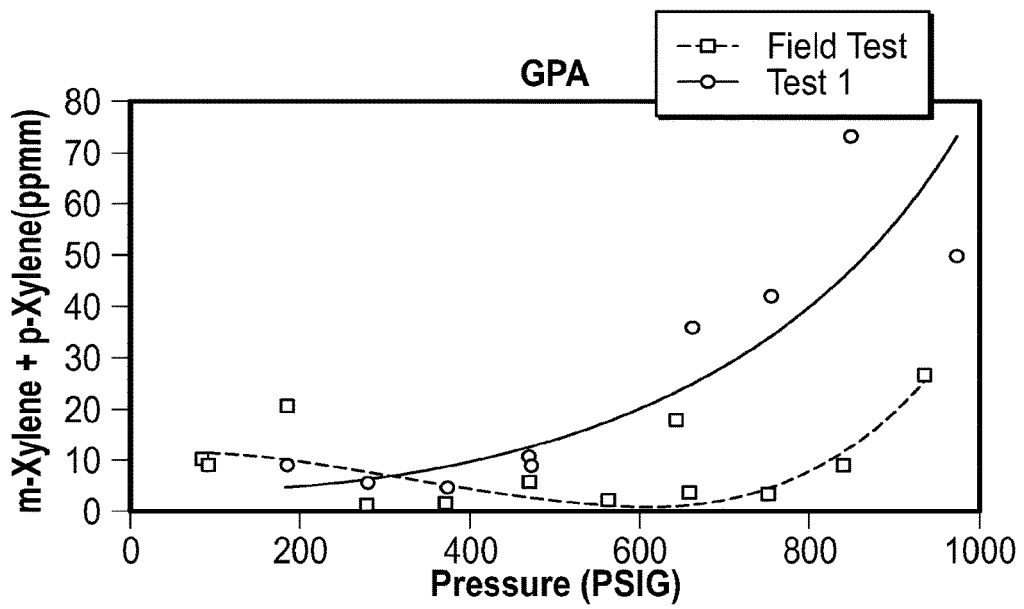
Figure 28:
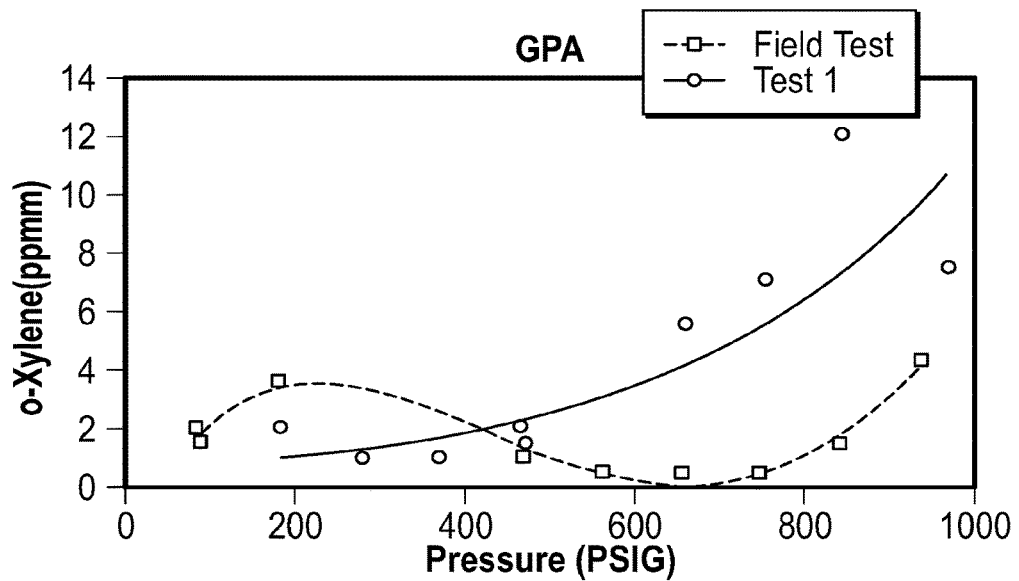
Figure 29:
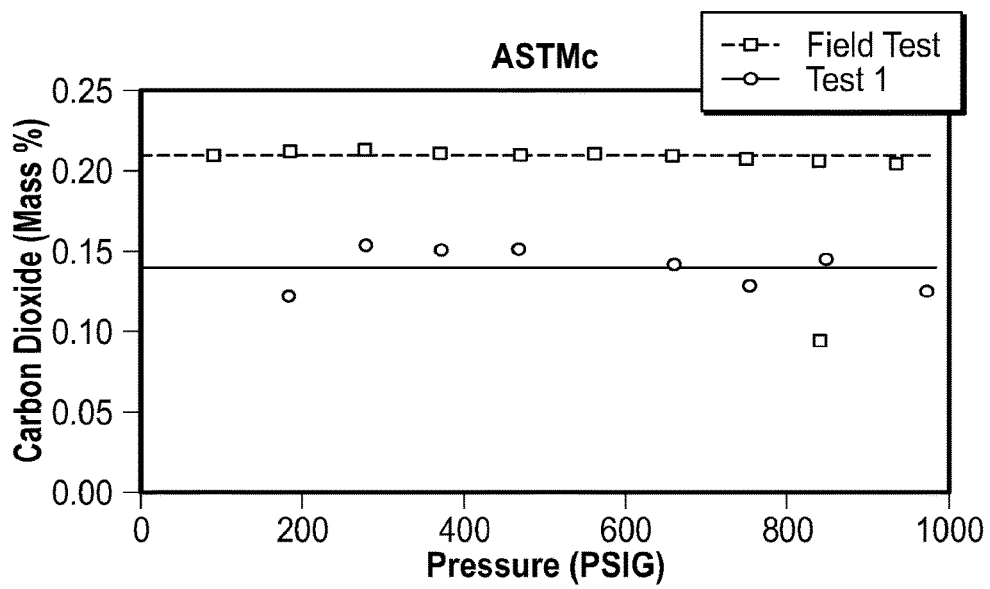
Figure 30:
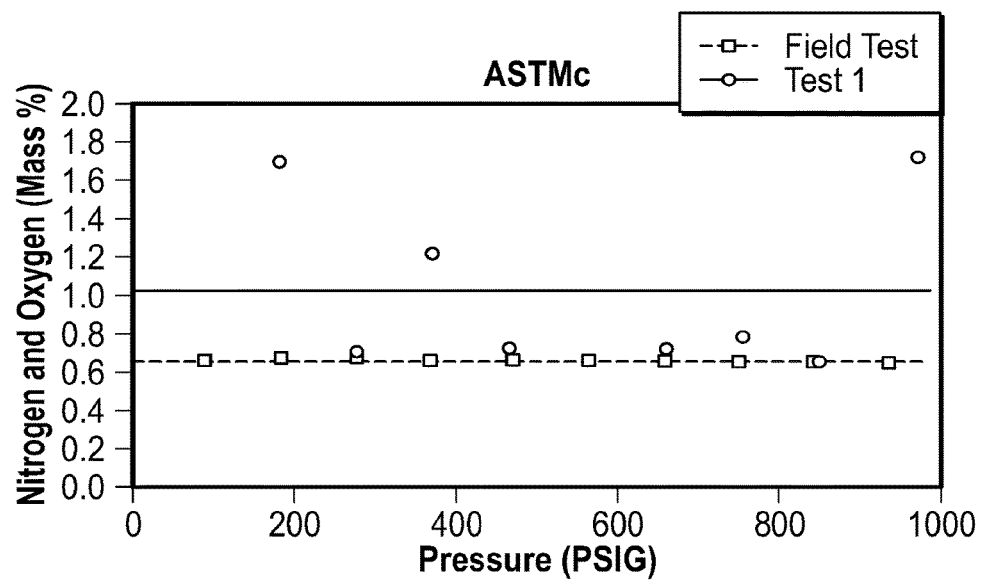
Figure 31:
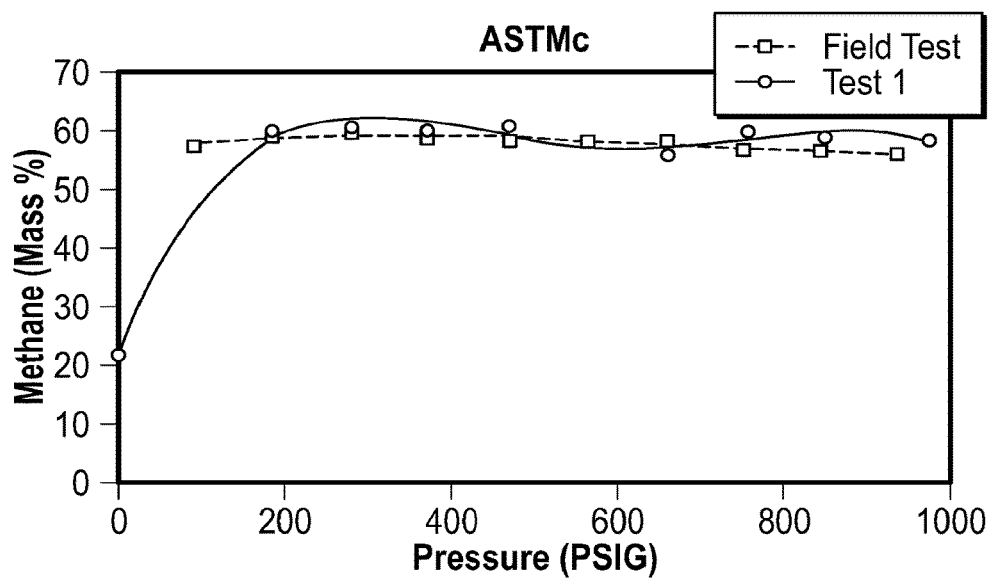
Figure 32:
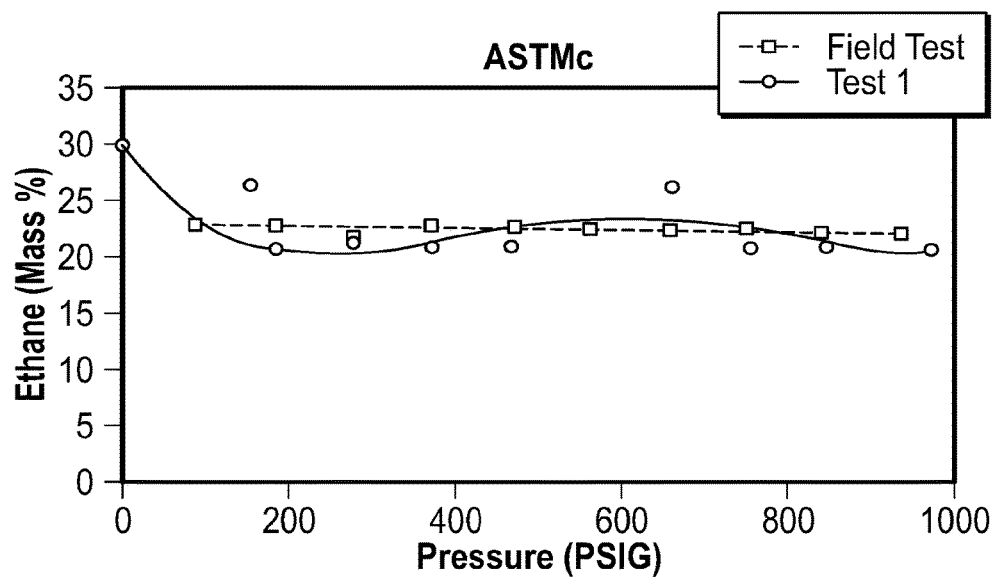
Figure 33:
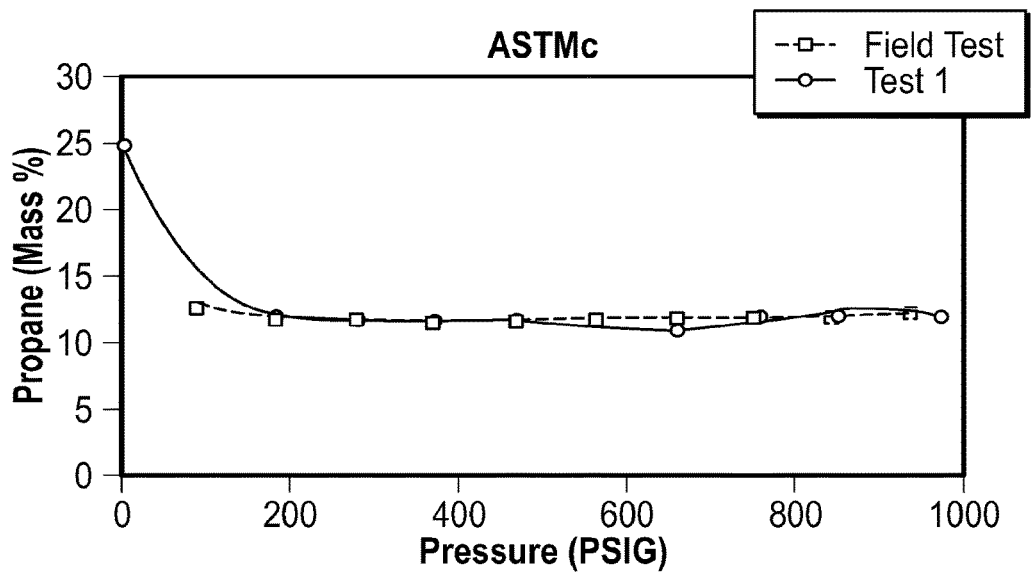
Figure 34:
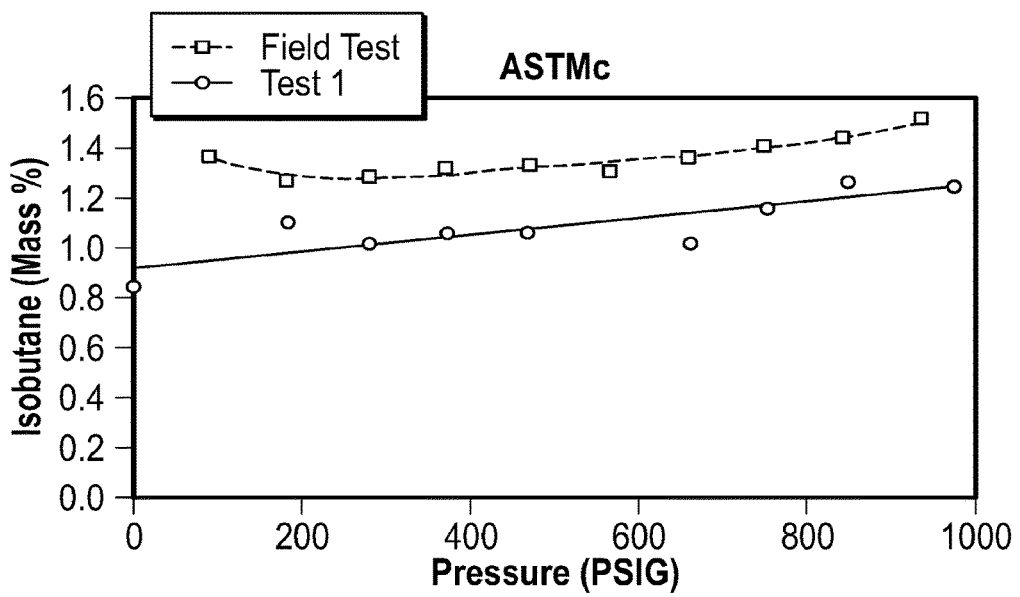
Figure 35:
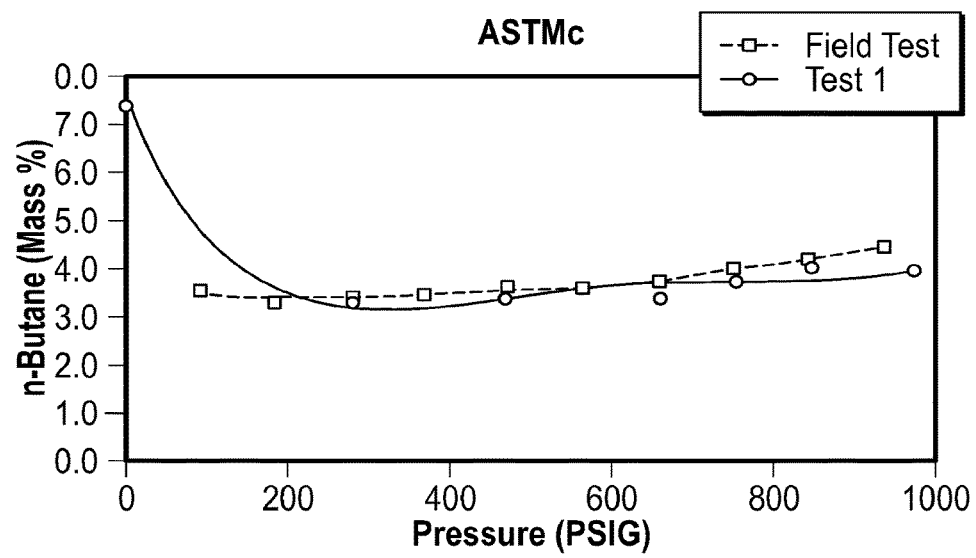
Figure 36:
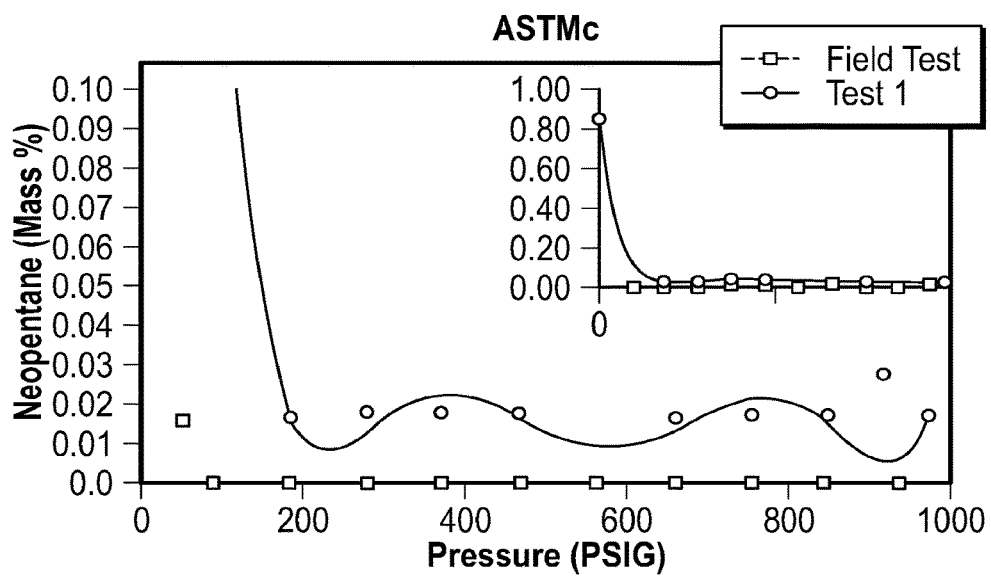
Figure 37:
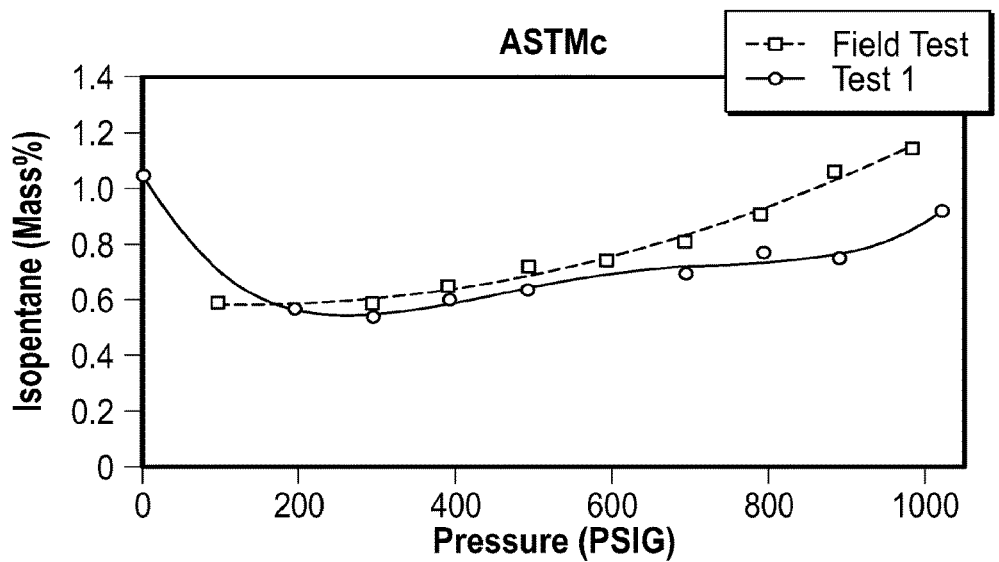
Figure 38:
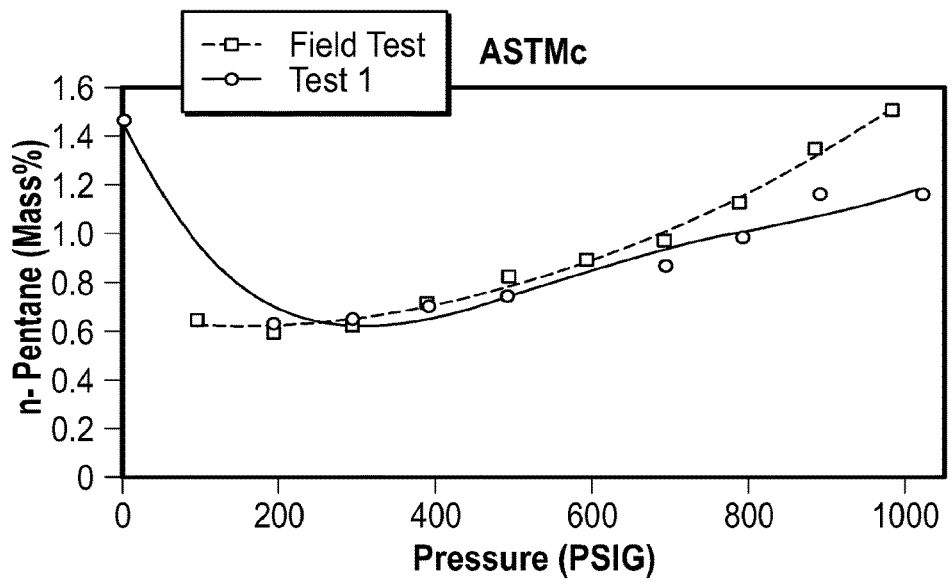
Figure 39:
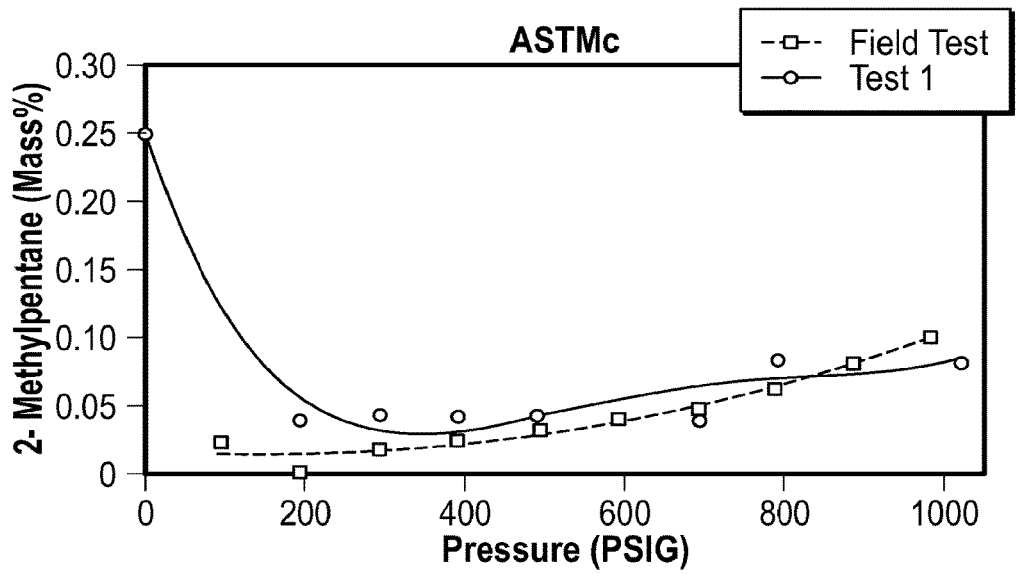
Figure 40:
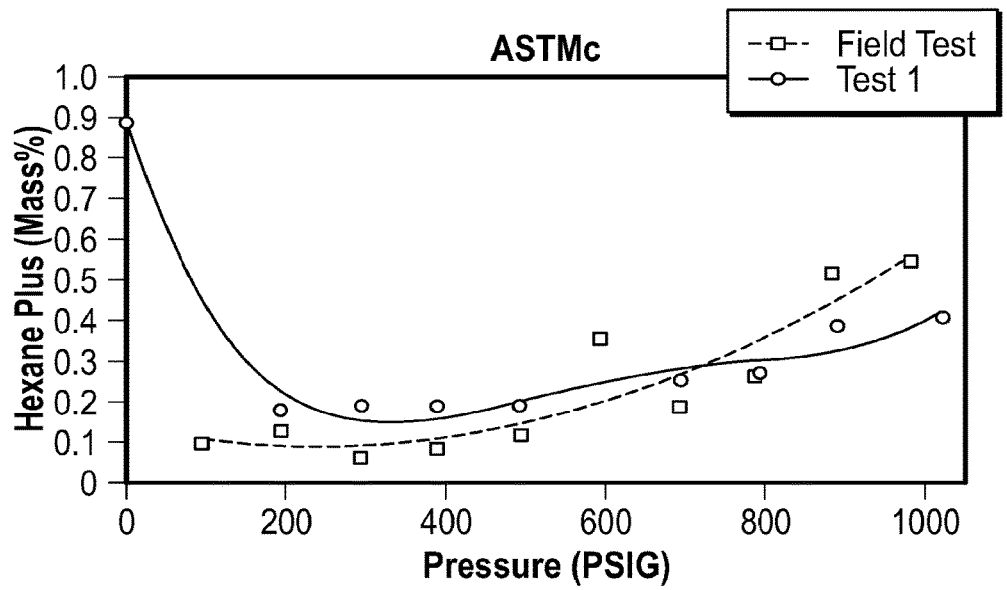
Figure 41:
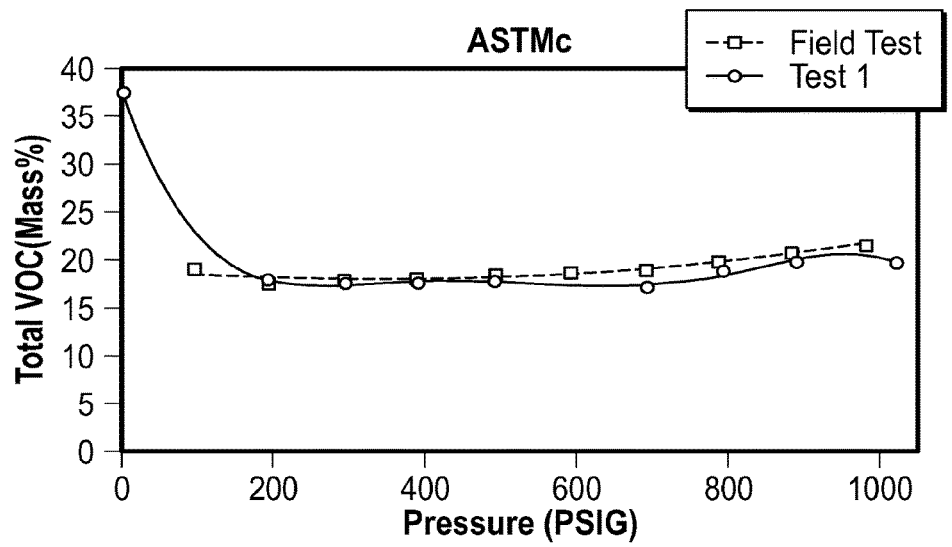
Figure 42:
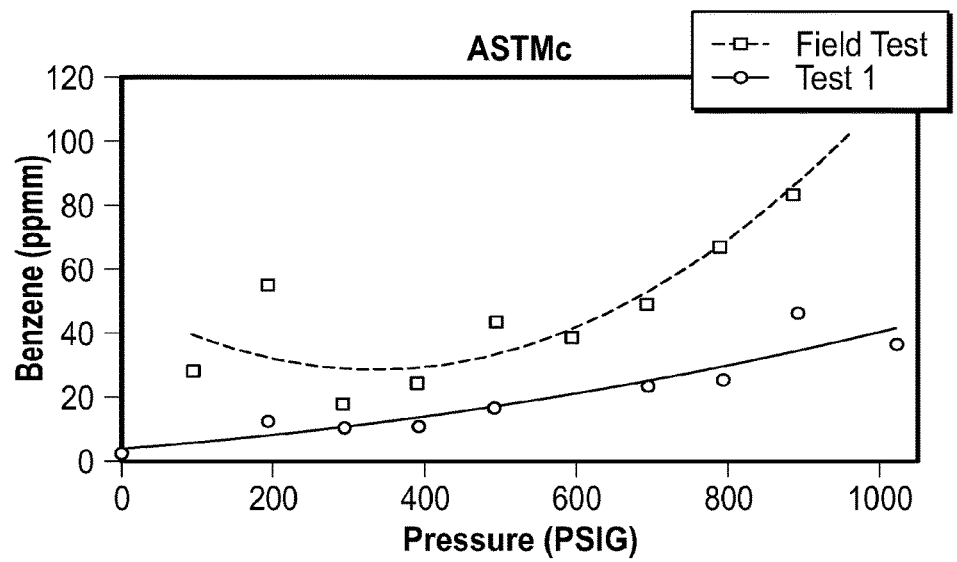
Figure 43:
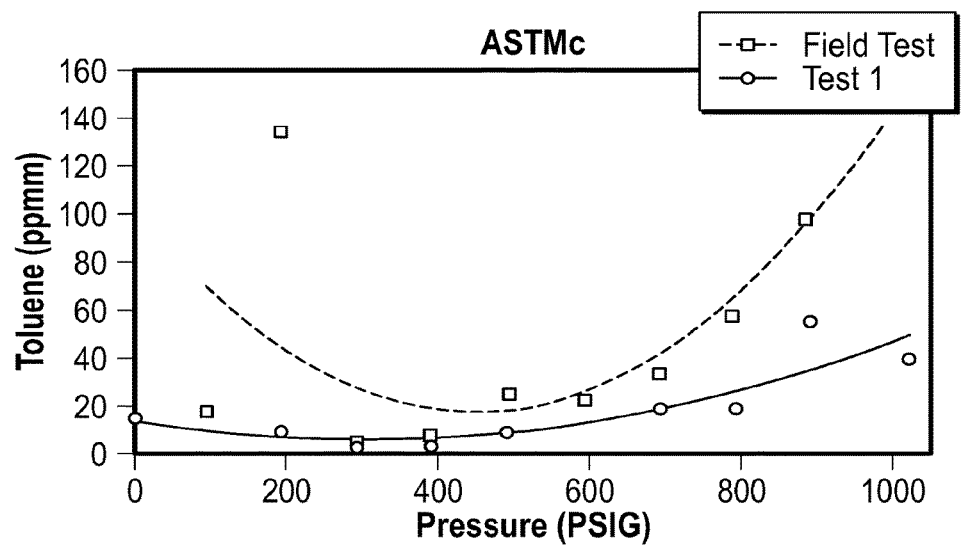
Figure 44:
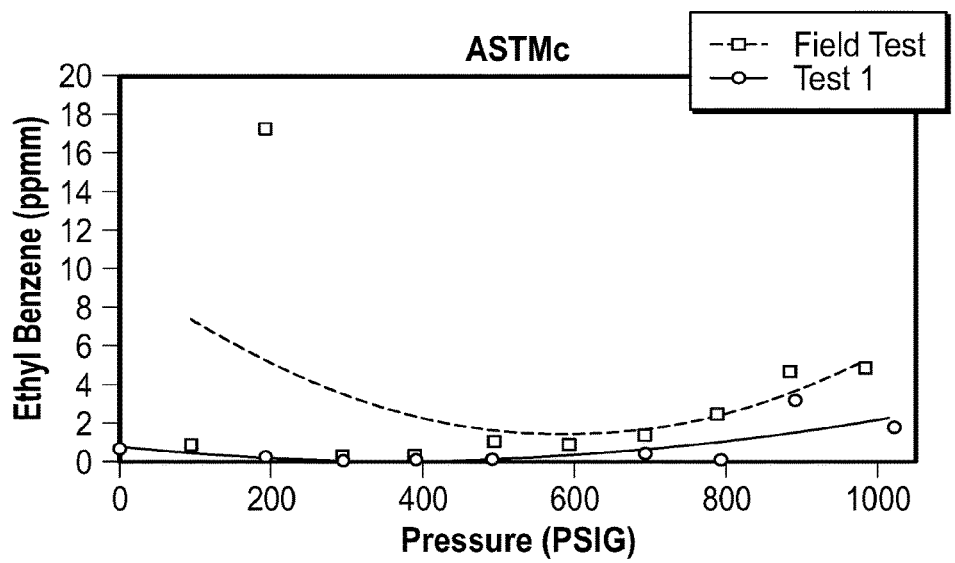
Figure 45:
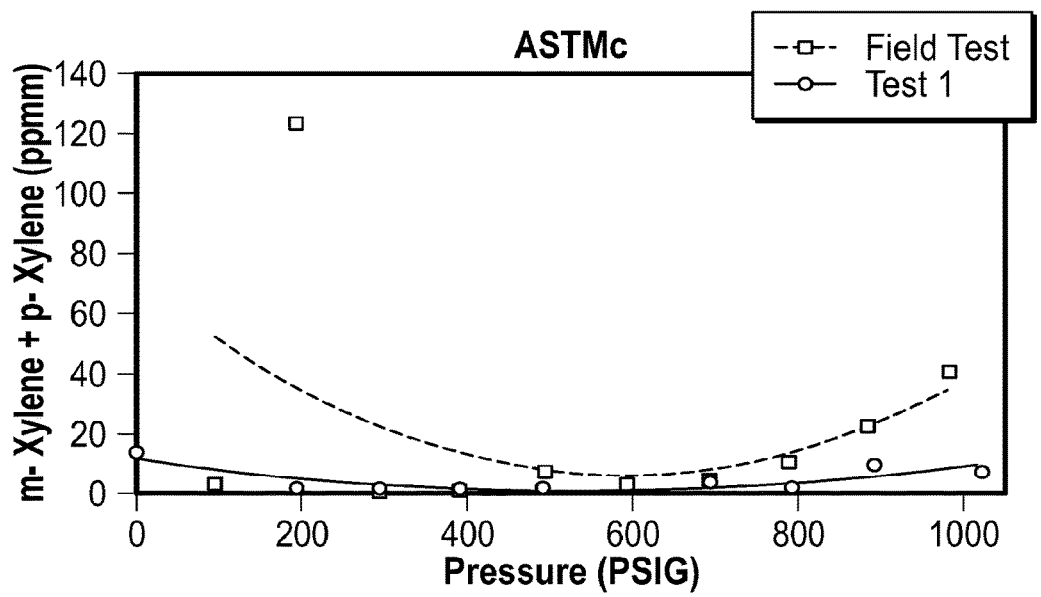
Figure 46:
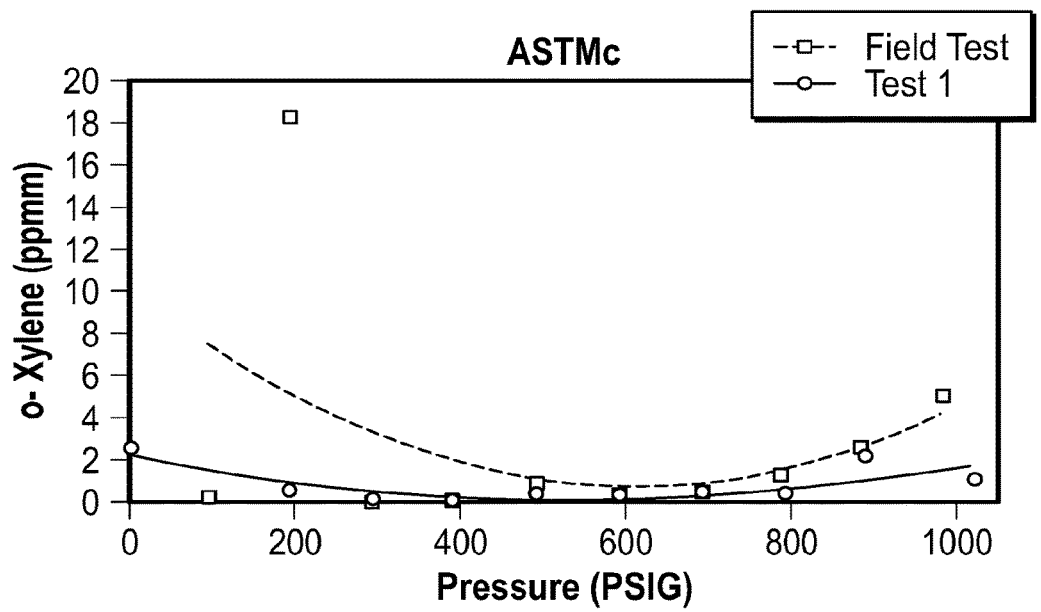

FIG. 7 illustrates the wiring diagram for a data acquisition and control system (DAC) 701, according to the embodiments shown in FIGS. 2 and 3. The DAC 701 is used for automation and may be located proximate to the pig receiver (not shown), e.g., within about 100 feet. The DAC 701 includes a controller 703 with 24-bit analog inputs, digital outputs, and 16-bit analog outputs. Pressure, temperature, mass flow rate, and density of the depressurization exhaust gas are logged by the DAC 701 as well as pressure of evacuated ambient pressure canisters and slip stream volumetric flow rate. Modules for the various components shown in FIGS. 2 and 3 can be seen in the DAC 701 wiring diagram of FIG. 7. For example, modules for digital outputs 705, analog outputs 707, and analog inputs 709 are shown. A series of steady state relays 711 receive the signals from digital outputs 705 and determine the state of a plurality of solenoid valves 713 (see related pneumatic valves 266, 366, 262, 362, 268, 368, 276, 376 on FIGS. 2 and 3). The analog output module 707 is provided to send signals to a flow control valve controller 717 to adjust flow control valve 360, 360 disposed in the slip stream/sampling line. The analog input module 709 is provided for the pressure sensors 714 (see analogous sensors 214, 314 on FIGS. 2 and 3), temperature sensors 712 (see analogous sensors 212, 312 on FIGS. 2 and 3), mass flow and mass density sensors 716 (see analogous sensors 216, 316 on FIGS. 2 and 3), a plurality of pressure sensors 774 (see analogous sensors 274, 374 on FIGS. 2 and 3) for the evacuated canisters 272, 372 (FIGS. 2 and 3), and volumetric flow meter 758 (see analogous flow meter 258, 358 on FIGS. 2 and 3) of the sampling line/slip stream 252, 352. A power module 715 is also provided. Electrical isolation components can be added between connections when required for safety. While FIG. 7 illustrates an exemplary embodiment of a DAC for use with the depressurization exhaust gas sampling systems of FIGS. 2 and 3, those skilled in the art will recognize that a similar DAC may be employed with the depressurization exhaust gas sampling system of FIG. 4.

In one or more embodiments, a custom cord (not shown) provides power from the DAC 701 to the Coriolis mass flow meter 216, 316 (FIGS. 2 and 3) and pressure, temperature, and vacuum gauges/sensors 212, 312, 214, 314, 274, 374 (FIGS. 2 and 3). This cord also connects the 4-20 mA signals from the Coriolis meter (mass flow rate and density), main line pressure gauge/sensor, temperature gauge/sensor, and evacuated canister assembly vacuum gauges/sensors to the controller 703 for data acquisition at 1 Hz. In one or more embodiments, 27 digital output channels (24 VDC) are used to actuate the pneumatic valves (see, e.g., valves 266, 366, 262, 362, 268, 368, 276, 376 on FIGS. 2 and 3) on the sample collection train 250, 350 (FIGS. 2 and 3). Activating a digital output channel 705 applies 24 VDC to a steady state relay 711 that closes a circuit to provide 110 VAC to change the position of a three-way solenoid valve 713. The inlets to all 27 DAC solenoid valves 713 can be connected to an inlet manifold (not shown) that is connected to a cylinder (not shown) that supplies nitrogen gas at approximately 90 psig. Opening a solenoid valve 713 directs nitrogen gas from the inlet of that solenoid valve 713 through a tube (in one or more embodiments, a 100 foot, ⅛ inch outer diameter tube) to a pneumatic isolation valve (see, e.g., valves 266, 366, 262, 362, 268, 368, 276, 376 on FIGS. 2 and 3) (i.e., opening the pneumatic valve) located in the sample collection train 250, 350 (FIGS. 2 and 3). Closing the solenoid valve 713 isolates the inlet of the solenoid valve so that the nitrogen gas does not pass through the solenoid valve to the tube and pneumatic valve and redirects the nitrogen gas in the tube to atmosphere (i.e., allowing the spring loaded pneumatic valve to close).

FIG. 3 shows automated components for the depressurization exhaust gas sampling system 300 according to various embodiments. The components of the depressurization exhaust gas sampling system 300 were discussed with reference to FIGS. 2 and 3. The illustrated data acquisition and control schematic diagram 701 (FIG. 7) shows digital outputs 705, analog inputs 709, and analog outputs 707, among other components. In an embodiment, the 27 digital outputs 705 labeled DO00-DO26 (FIG. 3) control the state of the pneumatic isolation valves (on/off valves). In an embodiment, the seven analog inputs labeled AI0-AI6 (FIG. 3) are 4-20 mA signals provided from select instruments to the controller and can be logged at 1 Hz. In an embodiment, the analog output labeled AO0 (FIG. 3) is a 4-20 mA signal to the sample collection train control valve 360 (FIG. 3) that determines the set point for the control valve 360 based on feedback from the sampling line flow meter 358 (labeled as AI2 on FIG. 3). Those skilled in the art will recognize that one or more computer programs or software, e.g., running on a dedicated or shared computer system, may be used to control the state of the various isolation valves (on/off) 266, 276, 366, 376 and flow control valve 360, 360 by sending programmed digital output signals 705 and analog output signals 707 responsive to analog input signals 706 received from one or more sensors 712, 714, 716, 774 and/or meters 758, as described above.

Although not part of every embodiment of the depressurization exhaust gas sampling system 200, 300, 400, it can be desirable, returning to FIG. 1, to characterize the liquid that is removed from pig receiver 106 after depressurization is complete. After pig receiver depressurization is complete and the receiver hatch 108 is opened, liquid can be collected in liquid trough or container 110. The mass and volume of each phase of the liquid can be measured using a gravimetric scale. Liquid trough or container 110, itself, may have volumetric measurements that allow for determination of the liquid volume. The temperature of the sub-surface liquid can be measured with a thermometer (not shown). These measurements can be repeated, for example, at hourly or other increments and as necessary to determine the long-term volatilization trend of the liquid in the container 110. Samples of the organic liquid caught in the receiver hatch liquid container 110 can be pipetted into a pre-weighed sample canister that can handle pressure increases from sample vaporization, and then weighed. If multiple phases of liquid are present, samples from each liquid phase can be obtained. Also, these samples can be obtained at hourly or other time increments and as necessary to determine the long-term volatilization trend. In one or more embodiments, the sample will be obtained as quickly as possible after the pig receiver 106 is drained to minimize bias from vaporization of more volatile compounds. Organic liquid samples may be obtained at hourly or other time increments as discussed above.

Thus, a method to characterize the liquid that is removed from pig receiver 106 after depressurization is complete may include: opening the receiver hatch 108 of in the pig receiver 106 after all pressured gas has been released from the pig receiver 106, collecting any liquids that are present in the pig receiver 106 in liquid trough or container 110, and analyzing the liquid collected in the liquid trough or container 110 to identify a mass amount of liquid that would evaporate at ambient temperature and pressure.

As previously described, only a portion of the exhaust gas flowing through exhaust gas line 104 during pig receiver depressurization is directed into the slip stream/sampling line 152. A more significant portion of the exhaust gas continues to flow downstream through exhaust gas line 104 and is throttled across valve 118. As best shown in FIG. 1, the throttled exhaust gas may be sent to a condensate knockout drum 124 to remove or separate out any condensed liquids into liquid container 123 and then the remaining throttled exhaust gas is directed to a flare 128 to be combusted. The post-combustion exhaust gas is emitted through vent 130. In one or more embodiments, the condensed liquids may be collected in a container 123 and the amount collected measured. Alternatively, the exhaust gas throttled across valve 118 may be emitted directly to atmosphere through vent 122 (e.g., for low pressured exhaust gas) or sent to gas recovery 120.

The methods, systems and apparatuses disclosed above with respect to the depressurization of a pig receiver may similarly be implemented to characterize emissions from the depressurization of a pig launcher.

Mass Emissions Calculations

The mass of gases (e.g., methane, ethane, alkanes ($C_1$-$C_9$+), select VOCs and select HAPs) that would be emitted or vented during pig receiver depressurization can be determined. According to one or more embodiments, the exhaust gas mass flow rate, temperature, and pressure, as well as the elapsed time from the depressurization start are automatically recorded. The composition of the gas collected in the grab samples or exhaust gas samples is determined and associated with each depressurization value (e.g., 100 psig) and may be further interpolated or extrapolated to achieve a composition versus pressure curve over the entire depressurization range (e.g., 1000 psig to approx. 0 psig). The composition versus pressure curve can then be used in conjunction with the mass flow rates to calculate the total mass of gas components in the exhaust gas. This calculation is described in more detail below.

In one or more embodiments, the instruments disposed in the exhaust gas line are spatially separated from the grab sample containers such that there is a time delay between the time of the mass flow rate, pressure, and temperature measurements and the time the grab samples are taken in the grab sample collection train. Thus, the elapsed time that is recorded when a grab sample is acquired can be corrected for the time delay for the exhaust gas to reach the grab sample containers. The standard volumetric flow rate at the sampling exhaust line can be measured using a flow meter 258, 358, 458 (FIGS. 2-4). The time delay between the grab samples and the main line measurements (t) is determined using the volumetric flow rate, pressure, temperature, and the sampling line volume between the main exhaust gas line 204, 304, 404 (FIGS. 2-4) and the grab sample containers (FIGS. 2-4), as shown in Equation 1:

$$t = L \cdot \pi \left(\frac{d_i}{2}\right)^2 \bigg/ \left(Q_S \cdot \frac{P_S}{P_A} \frac{T_A}{T_S}\right) \quad \text{Eq. 1}$$

In Equation 1, L is the length of the sampling line to the grab sample containers, $d_i$ is the inner diameter of the slip stream 252, 352, 452, and Q, P, T are the volumetric flow rate, pressure, and temperature of the gas, respectively, at standard (S) and actual conditions (A).

After correcting the grab samples for gas flow time delay, a model can be developed to describe mass concentration of each compound within the exhaust gas over the entire depressurization pressure range. For example, a polynomial curve can be used to fit the measured concentrations to pressure. The result of the model is a mass percent for each compound i at each pressure k ($C_{i,k}$, mass %). The $C_{i,k}$ value is multiplied by the measured depressurization mass flow rate ($\dot{m}_k$, lb/s) at pressure k to determine the mass flow rate of each compound at each pressure (Equation 2):

$$\dot{m}_{i,k} = \frac{C_{i,k}}{100} \dot{m}_k \quad \text{Eq. 2}$$

The total mass of each compound that is emitted during a depressurization event ($m_{i,dep}$, lb) is the sum of the product of mass emission rate and data logging time (t, s) over the sampling event using (Equation 3).

$$m_{i,dep} = \sum_{n=1}^{n} \dot{m}_{i,k} t \quad \text{Eq. 3}$$

Those skilled in the art will recognize that one or more computer programs or software, e.g., running on a dedicated or shared computer system, may be employed to determine the total mass of each compound that is emitted during pig receiver depressurization according to the methods disclosed herein. Further, those skilled in the art will understand that there are various, alternative methods and representations, e.g., the use of integrals, plotting data points to determine the area under a fitted curve, etc., that may be employed to determine the masses of individual gas compounds that are emitted during a depressurization event.

Thus, in an alternative embodiment, a method to determine the total component mass flow for each identifiable gas component in the exhaust gas from pig receiver depressurization may include:

analyzing each of the plurality of exhaust gas samples to identify a plurality of gas components;

determining a percentage of each gas component identified in each of the plurality of exhaust gas samples;

determining, for each of the plurality of exhaust gas samples, a component mass flow rate for each gas component identified by multiplying the percentage of each gas component in a particular exhaust gas sample by the mass flow rate associated with that particular exhaust gas sample;

determining, for a particular gas component, the component mass flow for each of the plurality of exhaust gas samples by multiplying the component mass flow rate by the sampling time period associated with each exhaust gas sample;

plotting, for the particular gas component, each of the component mass flows versus the elapsed times for each exhaust gas sample;

fitting a curve to the plotted component mass flows versus the elapsed times; and determining the area under the curve over a total elapsed time for pig receiver depressurization as the total component mass flow for the particular gas component during pig receiver depressurization.

Although not part of every embodiment, it can be desirable to determine the mass of alkanes ($C_1$-$C_9$+), select VOCs and select HAPs in the liquid obtained in the liquid collection container 110 (FIG. 1) as the receiver hatch 108 (FIG. 1) is opened after depressurization is complete. Compositional analysis of a sample of the liquid and the total liquid mass over time is used to calculate the mass of the potential emissions that would occur if this liquid was allowed to fully evaporate at ambient temperature and pressure.

The total mass of each gas that is emitted when the receiver hatch 108 (FIG. 1) is opened ($m_{i,rh}$, lb) is estimated using composition results from the lowest pressure grab sample and the ideal gas law (Equation 4). For this calculation, it is conservatively assumed that the entire volume of the pig receiver 106 (FIG. 1) is filled with gas at ambient pressure that has the composition of the lowest pressure grab sample. This method does not necessarily quantify the actual emissions from the receiver hatch 108 (FIG. 1), but provides a high threshold amount for these emissions. Actual emissions are expected to be lower than those predicted by this method.

$$m_{i,rh} = \frac{C_{i,0}}{100} \frac{PV}{RT} M_{w,g} \quad \text{Eq. 4}$$

In Equation 4, $C_{i,0}$=curve fit value for mass percent of component i at pressure of lowest pressure grab sample (psia), P=pressure (14.7 psia), V=Volume (ft$^3$), $$R = \text{ideal gas law constant} \left(\frac{\text{ft}^3 PSI}{°F \text{ mol}}\right),$$

T=Temperature (60° F.), and $M_{w,g}$ (lb/lb-mol) is the molecular weight of the gas determined from the lowest pressure grab sample.

Thus, alternatively stated, a method to determine the mass of the gas that may be emitted when opening the pig receiver hatch after pig receiver depressurization includes using volumetric dimensions of the receiver barrel and the temperature and pressure inside the receiver barrel as known variables in a gas law equation, such as the Ideal Gas Law, configured to solve for the mass of the gas. The individual gas component compositions may be assumed to be the same as or similar to those determined at the lowest pressure grab sample. Therefore, the mass of individual gas components that may be emitted when opening the pig receiver hatch after pig receiver depressurization may be determined by multiplying the total mass of the gas (as determined above using a gas law equation) by the individual gas component composition as determined from the lowest pressure grab sample.

Technology Demonstration and Proof of Concept Test Results

The above methods have been applied in two tests referred to herein as "Field Test" and "Test 1." These tests use the depressurization gas sampling system embodiment in FIGS. 2 and 3 to describe the mass emissions from a pig receiver and are provided as a demonstration of the depressurization sampling system. Laboratory analysis of gaseous grab samples was performed using a combination of standard approaches including GPA 2261, GPA 2286, and gas chromatograph mass spectrometer (GC-MS) (combined methods titled GPA) and a modified version of ASTM D7833 (ASTMc) that is described hereinafter.

The GPA and ASTMc lab analysis for alkanes (and inert gases) and BTEX for the Field Test and Test 1 are provided in FIGS. 8-11. Specifically, FIG. 8 provides GPA alkane (and inert gas) and BTEX results for the Field Test in a piston cylinder and evacuated canister embodiment, and FIG. 9 provides these results for the Test 1 test. FIG. 10 provides ASTMc alkane (and inert gas) and BTEX results for the Field Test in a piston cylinder and evacuated canister embodiment, and FIG. 11 provides these results for the Test 1 test. The general trends of the alkane analyses for the Field Test and Test 1 are that the alkane (non-methane) mol % decreases as pressure decreases from 1000 psig to approximately 100 psig. Then, the alkane mol % tends to increase as pressure decreases at pressures less than 100 psig. The inverse relationship between mol % and pressure was true for methane. The general trends of the BTEX analyses for the Field Test and Test 1 are that the BTEX volume percentage (ppmv) decreases as pig receiver pressure decreases from 1000 psig.

Real-Time Depressurization Potential Air Emissions

The real-time pressure, temperature, mass flow rate, and cumulative mass emissions for the vent gas from the pig receiver are provided in the set of graphs labeled as FIGS. 12A, 12B, 12C, and 12D. For both tests, the pressure decreases fairly linearly over 8-12 minutes from the starting pressure until the pressure is close to approximately 100 psig, when the depressurization exhaust flow is routed to the evacuated canisters. The pressure then decreases to approximately atmospheric pressure over the next approximately 3 minutes as the depressurization exhaust flow is ultimately routed to atmosphere. The temperature downstream of the pig receiver decreases during depressurization due to the Joule Thomson effect across the throttling valve near the pig receiver.

After depressurization flow has decreased (i.e., when pig receiver pressure is close to that of the pressure where it is being vented), temperature downstream of the pig receiver increases. Temperatures increase because the fluids in the pig receiver are warmed through heat transfer from the ambient environment.

The depressurization mass flow rate rapidly increases when the choke valve at the pig receiver vent is opened and then gradually decreases as the pressure decreases at a specific valve position until the pig receiver pressure reaches that of the ultimate vent.

Modeled Concentration of Air Emissions

The measured alkanes, inert gases, and BTEX from the GPA and ASTMc analyses of the Field Test and Test 1 along with the fitted model values are provided in FIGS. 13-46. Fitted model parameters and correlation coefficients are provided in FIGS. 47-54. Specifically, FIG. 47 provides the GPA model fitting parameters and correlation coefficients for alkane and inert gas mass % for the Field Test, and FIG. 48 provides the GPA model fitting parameters and correlation coefficients for BTEX mass % for the Field Test. FIG. 49 provides the GPA model fitting parameters and correlation coefficients for alkane and inert gas mass % for Test 1; and FIG. 50 provides the GPA model fitting parameters and correlation coefficients for BTEX mass % for Test 1. FIG. 51 provides the ASTMc model fitting parameters and correlation coefficients for alkane mass % for the Field Test; and FIG. 52 provides the ASTMc model fitting parameters and correlation coefficients for BTEX mass % for the Field Test. FIG. 53 provides the ASTMc model fitting parameters and correlation coefficients for alkane mass % for Test 1; and FIG. 54 provides the ASTMc model fitting parameters and correlation coefficients for BTEX mass % for Test 1. For Test 1, the 1.4 psig canister results are included in the respective Figures but were not used for fitting the models because they are leaner than the expected trends.

Total Potential Depressurization Emissions

A "Real Gas Law" model was used to estimate an upper limit for pig receiver emissions based on analysis of upstream pipeline gas and assumptions about the conditions in the pig receiver where the tests were performed. Benefits to using this method are that it allows for providing an upper limit emission estimate for comparison with measurements.

One of the key assumptions for this method is that the total mass of VOCs (i.e., combined gas and liquids) in the pig receiver is equal to the total mass of VOCs that are present in the same volume of pipeline at an upstream location (i.e., with upstream location pressure and assumed standard temperature of 60° F.). This assumption is expected to be conservative, because a portion of the VOCs condense in the pipeline before reaching the pig receiver resulting in a leaner VOC gas phase concentration in the pig receiver than the upstream location. Additionally, the pig receiver on which these tests were performed was purged before depressurization occurred. This would be expected to push the collected liquids downstream of the receiver such that only a small amount of liquid remains in the pig receiver due to low spots in the receiver and liquid trapped by the pig. Assuming the pig receiver gas is leaner than the upstream gas and that there is a small amount of VOC liquid in the receiver, the total mass of VOC in the receiver would be expected to be less than the amount that is calculated using upstream conditions.

Analysis of upstream pipeline gas is used to predict an upper limit for pig receiver gas VOC concentrations: specifically the molecular weight of the gas based on bulk concentration ($M_W$, lb/lb-mol) and the weight percent of each component i %). The upper limit for the mass of each VOC component in the pig receiver was then estimated through Equation 5:

$$m_i = \frac{PV}{RTZ} \frac{W_i}{100} \cdot M_W \qquad \text{Eq. 5}$$

where P=upstream pressure (psi), V=volume of pig receiver, $$R = \text{ideal gas law constant} \left(\frac{\text{ft}^3 PSI}{°R \text{ mol}}\right),$$

T=standard temperature basis for gas in the pig receiver (519.7° R, which is 60° F.), and Z=gas compressibility factor. The compressibility factor was calculated using the advanced Peng-Robinson equations-of-state as well as by using the Ref Prop 9 equations-of-state (via Virtual Materials Group VMG software).

The total potential depressurization emissions were directly measured with various embodiments disclosed herein and compared to the upper limit estimate based on the Real Gas Law model presented above. FIG. 55 includes the inputs and outputs for the equation of state Real Gas Law models.

The measured (using GPA and ASTMc lab analyses) and upper limit emissions estimates (using the Real Gas Law) for the Field Test and Test 1 are included in FIG. 56. For the Field Test and Test 1, the calculated alkane emissions were similar when using the GPA and ASTMc methods. This suggests the methods are comparable for alkane analysis.

The total VOC mass concentration values at each grab sample pressure determined from both the GPA and ASTMc analyses were averaged to determine a combined analysis model for each test. The uncertainty of the model was established as a function of pressure so that the modeled VOC mass concentration ±uncertainty provides a good fit to the data points. It should be emphasized that the VOC concentration uncertainty values were qualitatively determined but are believed to provide a conservative estimate.

The fitted model for VOC concentration ($m_{VOC}$, mass %) and uncertainty ($U_{mvoc}$, %) versus pressure (k, psig) determined based on results from both the GPA and ASTMc methods for the Field Test is provided in Equation 6.

$$\text{For } k < 89.8 \begin{cases} m_{VOC} = -10.64\ln(k) + 65.174 \\ \text{where } r^2 = 0.97 \\ U_{mvoc} = -0.0891 \cdot k + 12 \end{cases} \qquad \text{Eq. 6}$$

For $k \geq 89.8$ $$\begin{cases} m_{VOC} = 7.403 \cdot 10^{-11} \cdot k^4 - 1.596 \cdot 10^{-7} \cdot k^3 + 1.273 \cdot 10^{-4} \cdot \\ k^2 - 4.023 \cdot 10^{-2} \cdot k + 21.67 \\ U_{mvoc} = 4 \\ \text{where } r^2 = 0.99 \end{cases}$$

The fitted model for VOC concentration and uncertainty versus pressure determined based on results from both the GPA and ASTMc methods for Test 1 is provided in Equation 7. It should be noted that a single equation was used to model VOC concentration for the entire pressure range for Test 1.

$$m_{VOC} = -3.436 \cdot 10^{13} \cdot k^5 + 1.082 \cdot 10^{-9} \cdot k^4 - 1.305 \cdot 10^{-6} \cdot k^3 + 7.526 \cdot 10^{-4} \cdot k^2 \qquad \text{Eq. 7:}$$

where $r^2 = 1.0$
For k<97.1

$$\{U_{mvoc} = 0.2575 \cdot k + 30\}$$

For k≥97.1

$$\{U_{mvoc} = 4\}$$

Figure 59:
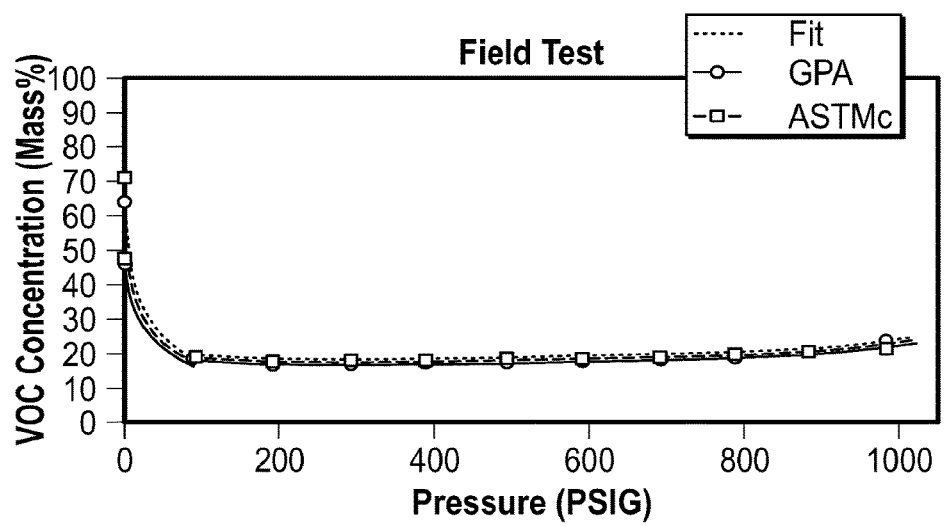
FIGS. 59-60 present graphical data of the measured mass concentrations for total VOCs using the GPA and ASTMc methods for two exemplary tests involving one or more embodiments disclosed herein, along with modeled mass concentrations based on results from both methods for the depressurization pressure range.
Figure 60:
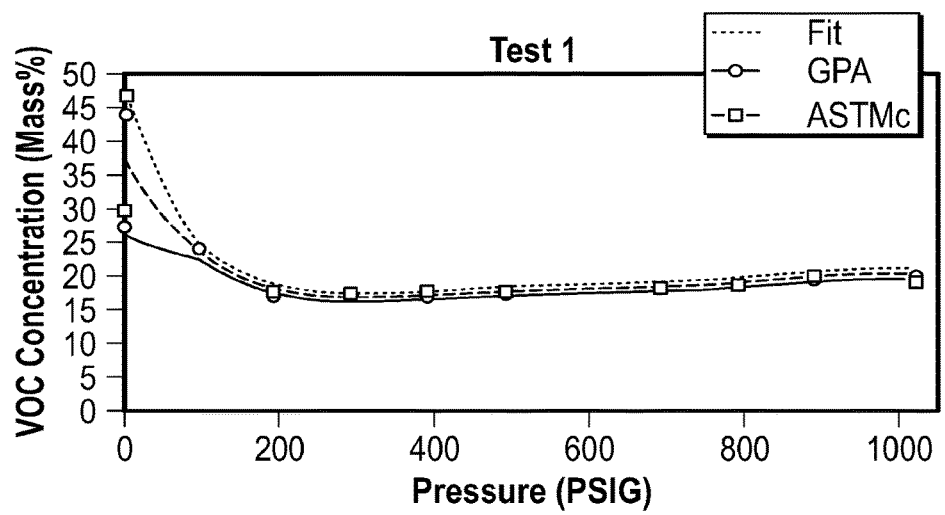

FIGS. 59 and 60 include the measured VOC concentration along with the pressure dependent model and uncertainty values from the above equations.

The combined lab analyses VOC concentration model and measured mass flow rates were used to determine the total VOC and mass emissions for each test along with uncertainties (FIG. 57). The combined GPA/ASTMc values for gas emissions values are within 25% and 20% of Real Gas Law estimates using the Advanced Peng Robinson and Ref Prop 9 equations, respectively (average absolute error values from FIG. 57). This result demonstrates a good agreement between the measured values and the upper limit estimates using known upstream gas properties, which further supports the measurement method and apparatus.

The total mass of gas and VOCs that remain in the pig receiver after depressurization is provided in FIG. 58. The assumptions for the values in FIG. 58 are that the entire volume of pig receiver is filled with an ideal gas with composition equivalent to the lowest pressure grab sample for each test at standard temperature and pressure. Although these values provide insight into the remaining mass in the pig receiver, they should not be considered emissions because the pig receiver hatch is opened for a short duration such that much of the mass in the pig receiver stays in the pig receiver (i.e., is not emitted to the atmosphere).

Analytical Methods for Grab Sample Analysis

Several analytical objectives are required to accurately characterize the grab samples obtained using embodiments disclosed herein. These include ensuring, to the greatest extent possible, that analytical results are free from biases due to interferents in the sample gas matrix, poorly resolved chromatographic peaks, and other causes. Another analytical objective is to ensure, to the greatest extent possible, that sample transfer procedures do not introduce unintentional biases into the analytical results. In addition, an analytical objective is to minimize the cost and oversight burden of the analytical procedures while maintaining the necessary quality and fitness of purpose of the analytical results.

The samples collected for this disclosure present certain analytical challenges that are difficult to address with standard analytical methods. One such analytical issue relevant to the collected gas samples is that some analytes of interest are present in high percent quantities while others are present at low ppm levels. Two analytical approaches (i.e., GPA and ASTMc), that address these challenges while providing high data quality with low resource usage, are disclosed:

Combination of Standard Natural Gas Analytical Methods (GPA)

Alkane and extended hydrocarbon analysis were performed using GPA 2261-95 and GPA 2286-95, respectively. The samples were then analyzed for BTEX using GC mass spectrometry (GC-MS). This analysis method is referred to herein as the GPA method.

Modified ASTM D7833-14 (ASTMc)

Various analytical approaches can be used to analyze grab samples with the disclosed embodiments. For example, in one or more embodiments, an analytical approach uses a modified version of ASTM D7833 for both hydrocarbon and air toxics compounds (ASTMc). The modified ASTM D7833 approach simultaneously provides percent level concentration of select hydrocarbons and ppmv level concentration of select trace analytes. The modifications to the standard method include: using a Porous Layer Open Tabular (PLOT) column for improved hydrocarbon peak resolution and using a post-column effluent split configuration that allows simultaneous detection from both an FID and MS. The MS can operate in the Selected Ion Monitoring (SIM) mode for analysis of BTEX components and select hydrocarbon components and the FID can be used for quantification of speciated hydrocarbons.

Other modifications include the use of an extended temperature range to allow for elution of BTEX compounds, the calibration for BTEX and selected hydrocarbons on each detector channel to cover the full analyte reporting ranges and allow for cross-validation of results for each detector, and the use of custom sample introduction protocol to accommodate the wide variety of sample pressures and avoid sample condensation during transfer.

This application is a continuation of, and claims priority to and the benefit of, U.S. Non-Provisional application Ser. No. 16/003,250, titled "SYSTEM, METHOD, AND APPARATUS FOR DETERMINING AIR EMISSIONS DURING PIG RECEIVER DEPRESSURIZATION," filed Jun. 8, 2018, which is a divisional of, and claims priority to and the benefit of, U.S. Non-Provisional application Ser. No. 15/626,109, titled "SYSTEM, METHOD, AND APPARATUS FOR DETERMINING AIR EMISSIONS DURING PIG RECEIVER DEPRESSURIZATION," filed Jun. 17, 2017, now U.S. Pat. No. 10,024,768, issued Jul. 17, 2018, which claims priority to and the benefit of U.S. Provisional Application No. 62/351,852, titled "SYSTEM, METHOD, AND APPARATUS FOR DETERMINING AIR EMISSIONS DURING PIG RECEIVER DEPRESSURIZATION," filed Jun. 17, 2016, and to U.S. Provisional Application No. 62/412,575, titled "SYSTEM, METHOD, AND APPARATUS FOR DETERMINING AIR EMISSIONS DURING PIG RECEIVER DEPRESSURIZATION," filed Oct. 25, 2016, the full disclosures of which are incorporated herein by reference.

The foregoing disclosure and description are illustrative and explanatory of various embodiments. Changes in the details of the illustrated embodiments can be made within the scope of the appended claims without departing from the true spirit of the inventive concept. Thus, the embodiments disclosed herein should be limited only by the following claims and their legal equivalents.

The invention claimed is:

1. A pipeline system to characterize emissions during pig receiver depressurization, the system comprising:
   a pipeline have a bore extending therethrough to provide a pathway for fluid flow and a terminus region;
   a pig receiver positioned in the terminus region of the pipeline and having a receiver barrel positioned to have a pipeline pig disposed therein, a receiver opening to provide access to the receiver barrel, and a receiver hatch positioned to cover the receiver opening;
   one or more exhaust gas lines in fluid communication with the pig receiver, each of the one or more exhaust gas lines having one or more slip streams in fluid communication therewith;
   one or more control valves positioned to control release of pressurized gas from the pig receiver as exhaust gas into the one or more exhaust gas lines, the one or more control valves being disposed in the one or more exhaust gas lines;
   one or more flow meters positioned to determine mass flow rate and exhaust pressure of the exhaust gas flowing through the one or more exhaust gas lines; and
   one or more gas analyzers positioned to analyze a plurality of exhaust gas samples obtained from the one or more slip streams over a range of different exhaust pressures when exhaust gas flows through the one or more exhaust gas lines and the one or more slip streams thereby to identify a plurality of gas components and determine a percentage of each gas component identified in each of the plurality of exhaust gas samples prior to removal of the pipeline pig from the pig receiver when positioned therein.

2. The system as defined in claim 1, wherein the pipeline pig comprises a device having an outer circumference less than an inner circumference of an inner wall of the pipeline that abuttingly moves along at least a portion of the inner wall of the pipeline when moved downstream within the pipeline by fluid flow, and wherein the pig receiver further comprises one or more piping arrangements selectively and fluidly coupled to the pipeline to receive the pipeline pig from the pipeline.

3. The system as defined in claim 1, wherein each of the one or more slip streams is positioned in fluid communication with the one or more exhaust gas lines upstream of the one or more control valves.

4. The system as defined in claim 1, further comprising a grab sample collection train positioned in fluid communication with the one or more slip streams, the grab sample collection train including a sampling manifold and a plurality of grab sample containers connected to the sampling manifold and positioned in fluid communication therewith, and whereby control of exhaust gas flow occurs through the sampling manifold of the grab sample collection train, and whereby the plurality of exhaust gas samples is supplied from the gas sample collection train to the one or more gas analyzers.

5. The system as defined in claim 4, further comprising one or more sampling exhaust lines positioned in fluid communication with the sampling manifold downstream of the plurality of grab sample containers, wherein the one or more control valves are positioned to control exhaust gas flow through the sampling manifold using the one or more control valves connected to the one or more sampling exhaust lines, and wherein the one or more gas analyzers includes one or more of a gas phase analyzer (GPA) and a mass spectrometer.

6. The system as defined in claim 5, wherein the one or more flow meters is disposed in the one or more sampling exhaust lines upstream thereof and is responsive to the one or more control valves.

7. The system as defined in claim 4, further comprising a data acquisition controller positioned to control the exhaust gas flow through the sampling manifold whereby the exhaust gas flow through the sampling manifold is less than the exhaust gas flow through the one or more exhaust gas lines.

8. The system as defined in claim 4, wherein the plurality of grab sample containers includes one or more piston cylinders and one or more evacuated canisters.

9. The system as defined in claim 4, wherein the plurality of grab sample containers includes one or more piston cylinders and one or more double-ended sampling cylinders.

10. The system as defined in claim 1, further comprising a liquid trough positioned to collect liquids present in the pig receiver, and whereby opening the receiver hatch of the pig receiver occurs after all pressurized gas has been released from the pig receiver, liquids present in the pig receiver are collected in the liquid trough, mass, volume and subsurface liquid temperature of collected liquids are determined, and a mass amount of liquid that would evaporate at ambient temperature and pressure is identified responsive to the liquids collected in the liquid trough.

11. The system as defined in claim 10, further comprising a condensate knockout drum positioned to remove condensed liquids from exhaust gas when throttled across the one or more control valves.

12. The system as defined in claim 10, wherein one or more of: the one or more flow meters and the one or more gas analyzers, are positioned to:
(a) determine, for each of the plurality of exhaust gas samples, a component mass flow rate for each gas component identified by multiplying the percentage of each gas component in a particular exhaust gas sample by the mass flow rate associated with that particular exhaust gas sample, (b) determine, for a particular gas component, the component mass flow for each of the plurality of exhaust gas samples responsive to component mass flow rate and sampling time period associated with each exhaust gas sample, and (c) determine total component mass flow for a particular gas component during pig receiver depressurization.

13. A pipeline system to characterize emissions during pig receiver depressurization, the system comprising:
a pipeline;
a pig receiver connected to the pipeline and having a receiver barrel positioned to have a pipeline pig disposed therein, a receiver opening to provide access to the receiver barrel, and a receiver hatch positioned to cover the receiver opening;
an exhaust gas line in fluid communication with the pig receiver, the exhaust gas line having a slip stream in fluid communication therewith;
a control valve positioned to control release of pressurized gas from the pig receiver as exhaust gas into the exhaust gas line, the control valve being disposed in the exhaust gas line;
a flow meter positioned to determine mass flow rate and exhaust pressure of the exhaust gas flowing through the exhaust gas line; and
a gas analyzer positioned to analyze a plurality of exhaust gas samples obtained from the slip stream over a range of different exhaust pressures when exhaust gas flows through the exhaust gas line and the slip stream thereby to identify a plurality of gas components and determine a percentage of each gas component identified in each of the plurality of exhaust gas samples when depressurizing the pig receiver.

14. The system as defined in claim 13, wherein the pipeline pig comprises a device having an outer circumference less than an inner circumference of an inner wall of the pipeline that abuttingly moves along at least a portion of the inner wall of the pipeline when moved downstream within the pipeline by fluid flow, and wherein the pig receiver further comprises one or more piping arrangements selectively and fluidly coupled to the pipeline to receive the pipeline pig from the pipeline.

15. The system as defined in claim 13, wherein slip streams is positioned in fluid communication with the exhaust gas line upstream of the control valve.

16. The system as defined in claim 13, further comprising a grab sample collection train positioned in fluid communication with the slip stream, the grab sample collection train including a sampling manifold and a plurality of grab sample containers connected to the sampling manifold and positioned in fluid communication therewith, and whereby control of exhaust gas flow occurs through the sampling manifold of the grab sample collection train, and whereby the plurality of exhaust gas samples is supplied from the gas sample collection train to the gas analyzer.

17. The system as defined in claim 16, further comprising a sampling exhaust line positioned in fluid communication with the sampling manifold downstream of the plurality of grab sample containers, wherein the control valve is positioned to control exhaust gas flow through the sampling manifold using the valve connected to the sampling exhaust line, and wherein the gas analyzer includes one or more of a gas phase analyzer (GPA) and a mass spectrometer.

18. The system as defined in claim 17, wherein the flow meter is disposed in the sampling exhaust lines upstream thereof and is responsive to the control valve.

19. The system as defined in claim 16, further comprising a data acquisition controller positioned to control the exhaust gas flow through the sampling manifold whereby the exhaust gas flow through the sampling manifold is less than the exhaust gas flow through the exhaust gas line.

20. The system as defined in claim 16, wherein the plurality of grab sample containers includes one or more piston cylinders and one or more evacuated canisters.

21. The system as defined in claim 16, wherein the plurality of grab sample containers includes one or more piston cylinders and one or more double-ended sampling cylinders.

22. The system as defined in claim 13, further comprising a liquid trough positioned to collect liquids present in the pig receiver, and whereby opening the receiver hatch of the pig receiver occurs after all pressurized gas has been released from the pig receiver, liquids present in the pig receiver are collected in the liquid trough, mass, volume and subsurface liquid temperature of collected liquids are determined, and a mass amount of liquid that would evaporate at ambient temperature and pressure is identified responsive to the liquids collected in the liquid trough.

23. The system as defined in claim 22, further comprising a condensate knockout drum positioned to remove condensed liquids from exhaust gas when throttled by activation of or across the control valve.

24. The system as defined in claim 22, wherein one or more of: the flow meters and the gas analyzer, are positioned to:
 (a) determine, for each of the plurality of exhaust gas samples, a component mass flow rate for each gas component identified by multiplying the percentage of each gas component in a particular exhaust gas sample by the mass flow rate associated with that particular exhaust gas sample, (b) determine, for a particular gas component, the component mass flow for each of the plurality of exhaust gas samples responsive to component mass flow rate and sampling time period associated with each exhaust gas sample, and (c) determine total component mass flow for a particular gas component during pig receiver depressurization.

\* \* \* \* \*